US012562237B2

(12) United States Patent
Zeng et al.

(10) Patent No.: US 12,562,237 B2
(45) Date of Patent: Feb. 24, 2026

(54) METHODS AND SYSTEMS FOR DETECTION AND PHASING OF COMPLEX GENETIC VARIANTS

(71) Applicant: Laboratory Corporation of America Holdings, Burlington, NC (US)

(72) Inventors: Qiandong Zeng, Burlington, NC (US); Natalia Tszine Leach, Burlington, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1309 days.

(21) Appl. No.: 17/324,793

(22) Filed: May 19, 2021

(65) Prior Publication Data

US 2021/0366575 A1    Nov. 25, 2021

Related U.S. Application Data

(60) Provisional application No. 63/026,948, filed on May 19, 2020.

(51) Int. Cl.
| | |
|---|---|
| *G16B 30/00* | (2019.01) |
| *C12Q 1/6874* | (2018.01) |
| *G16B 20/00* | (2019.01) |
| *G16B 20/20* | (2019.01) |

(52) U.S. Cl.
CPC ........... *G16B 30/00* (2019.02); *C12Q 1/6874* (2013.01); *G16B 20/00* (2019.02); *G16B 20/20* (2019.02)

(58) Field of Classification Search
CPC .................................................... G16B 30/00
See application file for complete search history.

(56) References Cited

U.S. PATENT DOCUMENTS

2016/0298185 A1    10/2016    Shukla et al.

FOREIGN PATENT DOCUMENTS

| | | |
|---|---|---|
| EP | 3 483 286 | 5/2019 |
| JP | 2019083781 A | 6/2019 |
| WO | 2015/085147 | 6/2015 |

OTHER PUBLICATIONS

Chowdhury B. et. al., "A review on multiple sequence alignment from the perspective of genetic algorithm" Genomics 109:419-431 (2017) (Year: 2017).*
Nik-Zainal S. et. al. "The Life History of 21 Breast Cancers" Cell 149:994-1007 (2012) (Year: 2012).*
VanLoo P. et. al. "Allele-specific copy number analysis of tumors" PNAS 107:16910-16915 (2010) (Year: 2010).*
Elyanow R. et. al. "Identifying structural variants using linked-read sequencing data" Bioinformatics 34(2):353-360 (2018) (Year: 2018).*

Sebastio G. et al. "The Molecular Basis of Homocystinuria Due to Cystathionine beta-Synthase Deficiency in Italian Families, and Report of Four Novel Mutations" Am. J. Hum. Genet. 56:1324-1333 (1995) (Year: 1995).*
Zhu H. et. al. "Cystathionine ◆◆ -Synthase in Physiology and Cancer" BioMed Research International 3205125, 11 pages, (2018) (Year: 2018).*
McKenna, A. et al., "The Genome Analysis Toolkit: a MapReduce framework for analyzing next-generation DNA sequencing data," *Genome Res* 20, 1297-1303 (2010).
Treangen, T. J. & Salzberg, S. L., "Repetitive DNA and next-generation sequencing: computational challenges and solutions," *Nat Rev Genet* 13, 36-46 (2011).
Brandt, D. Y. et al., "Mapping Bias Overestimates Reference Allele Frequencies at the HLA Genes in the 1000 Genomes Project Phase I Data," *G3 (Bethesda)* 5, 931-941 (2015).
Degner, J. F. et al., "Effect of read-mapping biases on detecting allele-specific expression from RNA-sequencing data," *Bioinformatics* 25, 3207-3212 (2009).
Lunter, G. and Goodson, M., "Stampy: a statistical algorithm for sensitive and fast mapping of Illumina sequence reads," *Genome Res* 21, 936-939 (2011).
Abecasis, G. R. et al., "An integrated map of genetic variation from 1,092 human genomes," *Nature* 491, 56-65 (2012).
Roach, J. C. et al., "Chromosomal haplotypes by genetic phasing of human families," *Am J Hum Genet* 89, 382-397 (2011).
Browning, S. R. and Browning, B. L., "Haplotype phasing: existing methods and new developments," *Nat Rev Genet* 12, 703-714 (2011).
Bracciali, A. et al., "PWHATSHAP: efficient haplotyping for future generation sequencing," *BMC Bioinformatics* 17, 342 (2016).
Patterson, M. et al., "WhatsHap: Weighted Haplotype Assembly for Future-Generation Sequencing Reads," *J Comput Biol* 22, 498-509 (2015).
Snyder, M. W. et al., "Haplotype-resolved genome sequencing: experimental methods and applications," *Nat Rev Genet* 16, 344-358 (2015).
Elyanow, R. et al., "Identifying structural variants using linked-read sequencing data," *Bioinformatics*, 34(2):353-360 (2017).
Van Dijk, E. L. et al., "The Third Revolution in Sequencing Technology," *Trends Genet* 34, 666-681 (2018).

(Continued)

*Primary Examiner* — Olivia M. Wise
*Assistant Examiner* — Francini Alvarenga Fonseca Lopez
(74) *Attorney, Agent, or Firm* — Kilpatrick Townsend & Stockton LLP

(57)    ABSTRACT

Disclosed are methods, systems and computer-program products for the determination of complex genetic variants. The disclosed methods, systems and computer-program products may include obtaining a mutant scaffold nucleotide sequence that comprises a sequence that includes mutations characteristic of the complex genetic variant; obtaining a wild-type scaffold nucleotide sequence having a wild-type sequence; generating an alignment of at least one sequence from the sample to the mutant scaffold and to the wild-type scaffold; and determining that the sample contains a mutation characteristic of the complex genetic variant based on alignment to the mutant scaffold and not the wild-type scaffold.

20 Claims, 9 Drawing Sheets

Specification includes a Sequence Listing.

(56)　　　　　References Cited

OTHER PUBLICATIONS

Romano, M. et al., "Origin and evolution of the c.844_845ins68/c.833T>C mutations within the cystathionine β-synthase gene in great apes," *FEBS Lett* 582, 423-426 (2008).

Skovby, F., et al., "A revisit to the natural history of homocystinuria due to cystathionine β-synthase deficiency," *Mol Genet Metab* 99, 1-3 (2010).

Auton, A. et al., "A global reference for human genetic variation," *Nature* 526, 68-74 (2015).

Karczewski, K. J. et al., "Variation across 141,456 human exomes and genomes reveals the spectrum of loss-of-function intolerance across human protein-coding genes," *bioRxiv*, 531210 (2019).

Sebastio, G. et al., "The molecular basis of homocystinuria due to cystathionine β-synthase deficiency in Italian families, and report of four novel mutations," *Am J Hum Genet* 56, 1324-1333 (1995).

Pepe, G. et al., "World distribution of the T833C/844INS68 CBS in cis double mutation: a reliable anthropological marker," *Hum Genet* 104, 126-129 (1999).

Landrum, M. J. et al., "ClinVar: improving access to variant interpretations and supporting evidence," *Nucleic Acids Res* 46, D1062-D1067 (2018).

Tsai, M. Y. et al., "High prevalence of a mutation in the cystathionine β-synthase gene," *Am J Hum Genet* 59, 1262-1267 (1996).

Kluijtmans, L. A. et al., "A common 844INS68 insertion variant in the cystathionine β-synthase gene," *Biochem Mol Med* 62, 23-25 (1997).

Chasse, J. F. and Barouki, R., "Characterisation of a human liver cystathionine beta synthase mRNA sequence corresponding to the c.[833T>C;844_845ins68] mutation in CBS gene," *Mol Cell Biochem* 332, 183-187 (2009).

Romano, M., "G runs in cystathionine B-synthase c.833C/c.844_845ins68 mRNA are splicing silencers of pathogenic 3' splice sites," *Biochim Biophys Acta* 1799, 568-574 (2010).

Huang, W. et al., "ART: a next-generation sequencing read simulator," *Bioinformatics* 28, 593-594 (2012).

DePristo, M. A. et al., "A framework for variation discovery and genotyping using next-generation DNA sequencing data," *Nat Genet* 43, 491-498 (2011).

Vyletal, P. et al., "Diversity of cystathionine beta-synthase haplotypes bearing the most common homocystinuria mutation c.833T>C: a possible role for gene conversion," *Hum Mutat* 28, 255-264 (2007).

Franco, R. F. et al., "Heterogeneous ethnic distribution of the 844ins68 in the cystathionine β-synthase gene," *Hum Hered* 48, 338-342 (1998).

Zhang, G. and Dai, C., "Gene polymorphisms of homocysteine metabolism-related enzymes in Chinese patients with occlusive coronary artery or cerebral vascular diseases," *Thromb Res* 104, 187-195 (2001).

Chen, J. et al., "Systematic comparison of germline variant calling pipelines cross multiple next-generation sequencers," *Sci Rep* 9, 9345 (2019).

Kishikawa, T. et al., "Empirical evaluation of variant calling accuracy using ultra-deep whole-genome sequencing data," *Sci Rep* 9, 1784 (2019).

Belsare, S. et al., "Evaluating the quality of the 1000 genomes project data," *BMC Genomics* 20, 620 (2019).

Robinson, J. T. et al., "Integrative genomics viewer," *Nat Biotechnol* 29, 24-26, (2011).

Grant et al., "Interrogating Mutant Allele Expression via Customized Reference Genomes to Define Influential Cancer Mutations", Scientific Reports 9(1):12766 (2019), 15 pages.

PCT/US2021/033177, International Search Report and Written Opinion, Sep. 10, 2021, 15 pages.

Office Action issued in JP2022-570551 dated May 16, 2025, 12 pages.

* cited by examiner

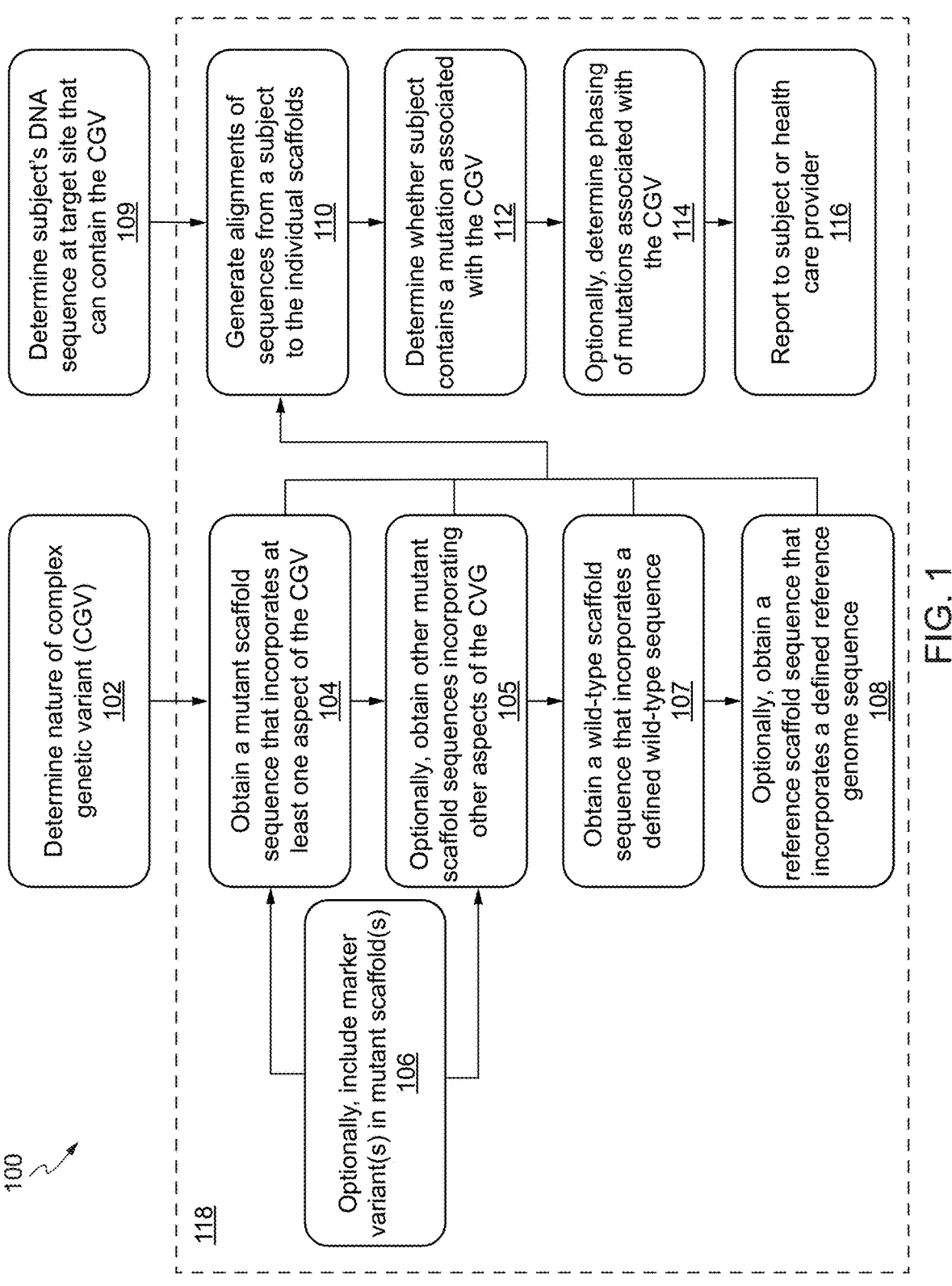

Determine subject's DNA sequence at target site that can contain the CGV
109

Generate alignments of sequences from a subject to the individual scaffolds
110

Determine whether subject contains a mutation associated with the CGV
112

Optionally, determine phasing of mutations associated with the CGV
114

Report to subject or health care provider
116

Determine nature of complex genetic variant (CGV)
102

Obtain a mutant scaffold sequence that incorporates at least one aspect of the CGV
104

Optionally, obtain other mutant scaffold sequences incorporating other aspects of the CVG
105

Obtain a wild-type scaffold sequence that incorporates a defined wild-type sequence
107

Optionally, obtain a reference scaffold sequence that incorporates a defined reference genome sequence
108

Optionally, include marker variant(s) in mutant scaffold(s)
106

CBS wild-type sequence

Intron7
...tctgaggctgggaacaggccaccaccccacaggcagatcattaacaggcagttgttaacggcggtattggccactccatatagaatatcgaggc Exon8
atgtccaggcggggctttgctgctgagccctgaagccgcgccctgagccctgaagccgcgccctgagccctgaagccgcgccctgagcagATCATTGGGGTGGATCCCGAAGGTCCATCCTCGCAGAGCCGGA
       833              844_845

Intron8
GGAGCTGAACCAGCAGGAGGAGCAGCAACCTACGAGGTGGAAGGGATCGGCTACGACTTCATCCCACGGTGCTGGACAGGACGgtaggtcgagtcc...

CBS c.[833T>C; 844_845ins68]

...cctctgcagATCATTGGGGTGGATCCCGaagccgcccctgagccctgggggctttgctgctgggcttgagcccctgaagccgcgccctgagccctgggggcttttgctgggctggcttcaggtgggcatccaggtgggggcttttgctgctgggcttgagcccctgaagccgcgccctgcagATCATTGGGGTGGATCCCG
  833              844                      833       844_845

CBS c.832_833ins68

...cctctgcagATCACTGGGGTGGATCatccaggtgggggcttttgctgctgggcttgagcccctgaagccgcgccctctcgcagATCACTGGGGTGGATCCCG
  832                                        833       844_845

FIG. 2A

SEQUENCE LISTING

```
<160> NUMBER OF SEQ ID NOS: 12

<210> SEQ ID NO 1
<211> LENGTH: 288
<212> TYPE: DNA
<213> ORGANISM: Homo sapiens

<400> SEQUENCE: 1
tctgaggctg ggaacaggcc accacccaca ggcagatcat taacaggcag ttgttaacgg      60
cggtattggc cactcccata atagaatatc gaggcatgtc caggcggggc ttttgctggc     120
cttgagccct gaagccgcgc cctctgcaga tcattggggt ggatcccgaa gggtccatcc     180
tcgcagagcc ggaggagctg aaccagacgg agcagacaac ctacgaggtg gaagggatcg     240
gctacgactt catccccacg gtgctggaca ggacggtagg tcgagtcc                  288

<210> SEQ ID NO 2
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cctctgcaga tcactggggt ggatcatcca ggtggggctt ttgctgggct tgagccctga      60
agccgcgccc tctgcagatc attggggtgg atcccg                                96

<210> SEQ ID NO 3
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctctgcaga tcactggggt ggatcatcca ggtggggctt ttgctgggct tgagccctga      60
agccgcgccc tctgcagatc attggggtgg atcccg                                96
```

-continued

```
<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtaaaacga cggccagtcc accacccaca ggcagat                               37

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggaaacag ctatgaccgc ggggcttgcc cttctgtt                              38

<210> SEQ ID NO 6
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgggatccac cccaatgatc tgcagagggc gcggcttcag cgctcaagcc cagcaaaagc      60
cccacctgga tgatccaccc caatgatctg c                                     91

<210> SEQ ID NO 7
<211> LENGTH: 91
<212> TYPE: DNA
<213> ORGANISM: Homo sapiens

<400> SEQUENCE: 7
cgggatccac cccaatgatc tgcagagggc gcggcttcag ggctcaaggc cagcaaaagc      60
cccgcctgga catgccacga tattctatta t                                     91

<210> SEQ ID NO 8
<211> LENGTH: 91
<212> TYPE: DNA
<213> ORGANISM: Homo sapiens

<400> SEQUENCE: 8
cgggatccac cccaatgatc tgcagagggc gcggcttcag cgctcaaggc cagcaaaagc      60
cccgcctgga catgcctcga tattctatta t                                     91

<210> SEQ ID NO 9
<211> LENGTH: 91
<212> TYPE: DNA
<213> ORGANISM: Homo sapiens

<400> SEQUENCE: 9
cgggatccac cccaatgatc tgcagagggc gcggcttcag ggctcaaggc cagcaaaagc      60
cccgcctgga catgcctcga tattctatta t                                     91

<210> SEQ ID NO 10
```

-continued

```
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgggatccac cccaatgatc tgcagagggc gcggcttcag ggctcaaggc cagcaaaagc        60
cccacctgga tgatccaccc caatgatctg c                                       91

<210> SEQ ID NO 11
<211> LENGTH: 91
<212> TYPE: DNA
<213> ORGANISM: Homo sapiens

<400> SEQUENCE: 11
cgggatccac cccaatgatc tgcagagggc gcggcttcag ggctcaaggc cagcaaaagc        60
cccacctgga catgcctcga tattctatta t                                       91

<210> SEQ ID NO 12
<211> LENGTH: 78
<212> TYPE: DNA
<213> ORGANISM: Homo sapiens

<400> SEQUENCE: 12
cgggatccac cccaatgatc tgcagagggc gcggcttcag ggctcaaggc cagcaaacgc        60
cccgcctgga catgcctc                                                      78
```

METHODS AND SYSTEMS FOR DETECTION AND PHASING OF COMPLEX GENETIC VARIANTS

CROSS-REFERENCE TO RELATED APPLICATION

The present application is a non-provisional application of, and claims the benefit and priority under 35 U.S.C. 119(e) of U.S. Provisional Application No. 63/026,948, filed May 19, 2020, entitled "METHODS AND SYSTEMS FOR DETECTION AND PHASING OF COMPLEX GENETIC VARIANTS". The entire contents of the aforementioned application is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Jul. 30, 2021, is named 057618-1242779_SL.txt and is 3,588 bytes in size.

FIELD

This disclosure relates to methods and systems for detection and phasing of complex genetic variants.

BACKGROUND

Next-generation sequencing (NGS) refers to a process of massively parallel sequencing that produces a large number of target sequence reads. This technology has been widely used in the genetic diagnostics field as it enables simultaneous and rapid assessment of many clinically relevant genomic regions in patient samples. Variant identification is generally done by aligning sequence reads to a genomic reference in order to assess the presence of any sequence variations, and its analytical sensitivity in variant detection depends greatly on read mapping accuracy. NGS variant detection using short reads (e.g., Illumina sequencing) works well for point mutations, small insertions and deletions (indels), but has limitations in the detection of structural variants and variants residing in repetitive or highly homologous sequences. Even with the most recent human genome builds, GRCh37/HG19 and GRCh38/HG38, which include some alternative loci for highly divergent regions, most aligners are constrained to using one primary sequence as reference. As a result, sample reads that vary greatly from the reference may map either incorrectly or not at all. This reference bias affects the sensitivity and specificity of variant detection, resulting in false positive and false negative calls.

Variant phasing is used to identify whether two variants are located within the same copy of a chromosome (cis) or in two different copies (trans) as a compound heterozygote. Phasing information is imperative for predicting clinical consequences, especially in autosomal recessive disorders. Approaches that statistically infer phasing; i.e., population- or pedigree-based methods, require large cohorts or availability of generational family members for testing, and could be inapplicable to detect rare or de novo mutations. With NGS, algorithms for read-based phasing have been developed to computationally assemble overlapping reads with two or more heterozygous variants in target regions into larger haplotype blocks. NGS platforms for long-read sequencing can link multiple variants in one sequence read, thereby providing direct phasing information; however, the high cost, low throughput and high per-base error rate have restricted their use in clinical genetic testing. Linked-read sequencing can computationally build and phase long haplotypes at low error rate, but may have limited sensitivity in the detection of small structural variants and has mainly been used in genome phasing. In cases of structural variants, genome reference bias can further confound the phasing of even closely linked alleles due to faulty mapping. Thus, there is a need for improved methods and systems for detection and characterization of complex genetic variants.

SUMMARY

Disclosed are methods and systems that employ a custom scaffold approach for detecting and/or phasing genetic variants by next generation sequencing. The methods and systems may be embodied in a variety of ways.

In various embodiments, disclosed is a method for detecting the presence or absence of a complex genetic variant in a sample, comprising: (a) obtaining a mutant scaffold nucleotide sequence that comprises a sequence that includes mutations characteristic of the complex genetic variant; (b) obtaining a wild-type scaffold nucleotide sequence having a wild-type sequence; (c) generating an alignment of at least one sequence from the sample to the mutant scaffold and to the wild-type scaffold; and (d) determining that the sample contains a mutation characteristic of the complex genetic variant based on alignment to the mutant scaffold and not the wild-type scaffold.

In various embodiments, disclosed is a method for detecting the presence or absence of a complex genetic variant in a sample, comprising: obtaining a mutant scaffold that comprises a sequence that includes a mutation characteristic of the complex genetic variant within a target region of a genome; obtaining a wild-type scaffold that comprises a wild-type sequence within the target region of the genome; sequencing, by a massively parallel sequencer, nucleic acid from the sample for the target region that generates sequence reads; mapping, by a computing device using an alignment algorithm, the sequence reads to matching sequences that include the complex genetic variant sequence in the mutant scaffold; mapping, by the computing device using the alignment algorithm, the sequence reads to matching sequences that include the wild-type sequence in the wild-type scaffold; counting, by the computing device, the sequence reads mapped to the sequences that include the complex genetic variant sequence and the sequence reads mapped to the sequences that include the wild-type sequence, wherein the counting generates a quantification of the sequence reads mapped to the sequences that include the complex genetic variant sequence and a quantification of the sequence reads mapped to the sequences that include the wild-type sequence; determining, by the computing device, whether the sample contains the mutation based on the quantification of the sequence reads mapped to the sequences that include the complex genetic variant sequence versus the quantification of the sequence reads mapped to the sequences that include the wild-type sequence; and outputting, by the computing device, a result that the sample contains the presence or absence of the complex genetic variant based on the determination of whether the sample contains the mutation.

In some embodiments, the mutant scaffold further comprises an additional artificial genetic variation not found in either the complex variant sequence or the wild type sequence; the additional artificial genetic variation serves as a marker for the presence and/or phasing of the mutation characteristic of the complex genetic variant; mapping the sequence reads to matching sequences that include the complex genetic variant sequence in the mutant scaffold comprises identifying an expected mismatch between the sequence reads and the matching sequences that include the complex genetic variant sequence based on the additional artificial genetic variation; and the counting the sequence reads mapped to the sequences that include the complex genetic variant sequence includes counting the sequence reads mapped to the sequences that include the complex genetic variant sequence and the additional artificial genetic variation.

In some embodiments, the method further comprise parametrizing the alignment algorithm with a mismatch and gap penalty cost difference such that only the sequence reads that have the mutation characteristic of the complex genetic variant will align to the mutant scaffold.

In some embodiments, the method further comprises determining, by the computing device, the sample contains the mutation characteristic of the complex genetic variant based on the quantification of the sequence reads mapped to the sequences that include the complex genetic variant sequence versus the quantification of the sequence reads mapped to the sequences that include the wild-type sequence; outputting, by the computing device, the result that the sample contains the presence of the complex genetic variant based on the determination that the sample contains the mutation characteristic of the complex genetic variant; and providing a treatment to a subject associated with the sample in accordance with the presence of the complex genetic variant in the sample.

In some embodiments, the treatment is a therapeutic agent or a prescribed dietary change.

In some embodiments, the therapeutic agent is vitamin B6 or the dietary change is a low-methionine diet.

In some embodiments, the complex variant sequence has two mutations.

In some embodiments, the method further comprises: determining whether the two mutations are on the same chromosome (cis) or on different chromosomes (trans) based on the mapping of the sequence reads to the matching sequences in the mutant scaffold; and outputting, by the computing device, the result that the sample contains the presence or absence of the complex genetic variant with notation concerning the two mutations being on the same chromosome (cis) or on different chromosomes (trans) based on the determination of whether the sample contains the mutation characteristic of the complex genetic variant and whether the two mutations are on the same chromosome (cis) or on different chromosomes (trans).

In some embodiments, the complex genetic variant is in the target region of a cystathionine beta-synthase (CBS) gene.

In some embodiments, the mutant scaffold and wild-type scaffold distinguish (i) a sequence having a 68 bp insertion [844_845 ins68] in cis with a c.833T>C mutation, from (ii) a sequence having the 68 bp insertion [844_845 ins68] in trans with c.833T>C, from (iii) a sequence having the 68 bp insertion [844_845 ins68] without c.833T>C, or from (iv) a sequence having c.833T>C without the 68 bp insertion [844_845 ins68].

In various embodiments of the methods, systems and computer-program products, the custom scaffolds are in silico scaffolds.

Also disclosed herein are systems and/or kits that comprise such custom scaffolds for haplotype separation and if needed, a designed base change(s) to serve as the variant readout according to the methods disclosed herein. For example, disclosed is a system comprising: one or more data processors; and a non-transitory computer readable storage medium containing instructions which, when executed on the one or more data processors, cause the one or more data processors to perform actions including any of the method steps disclosed herein. Also disclosed is a computer-program product tangibly embodied in a non-transitory machine-readable storage medium, including instructions configured to cause one or more data processors to perform actions including any of the method steps disclosed herein.

BRIEF DESCRIPTION OF THE FIGURES

FIG. 1 shows a method for detection of complex variants in accordance with an embodiment of the disclosure.

FIG. 2a and FIG. 2b shows CBS c.833T>C and the complex variant, c.[833T>C; 844_845ins68] on chromosome 21 in accordance with an embodiment of the disclosure. Thus, FIG. 2a shows the wild-type sequence (FIG. 2a) (SEQ ID NO:1), the CBS c. [833T>C; 844-845ins68] sequence with both mutations on the same DNA (SEQ ID NO:2) and the CS c832-833ins68 (SEQ ID NO:3). FIG. 2b shows the normal allele, the CBS c.833T>C, and the complex variant, c.[833T>C; 844_845ins68] on chromosome 21 (FIG. 2b).

FIG. 3 discloses SEQ ID NOS 6, 7 and 7, respectively, in order of appearance.

FIG. 6 discloses SEQ ID NOS 6, 8, 8, 6, 9 and 9, respectively, in order of appearance.

FIG. 7 discloses SEQ ID NOS 6, 9 and 9, respectively, in order of appearance.

FIG. 8 discloses SEQ ID NOS 10-12, respectively, in order of appearance.

DETAILED DESCRIPTION

Figure 2B:
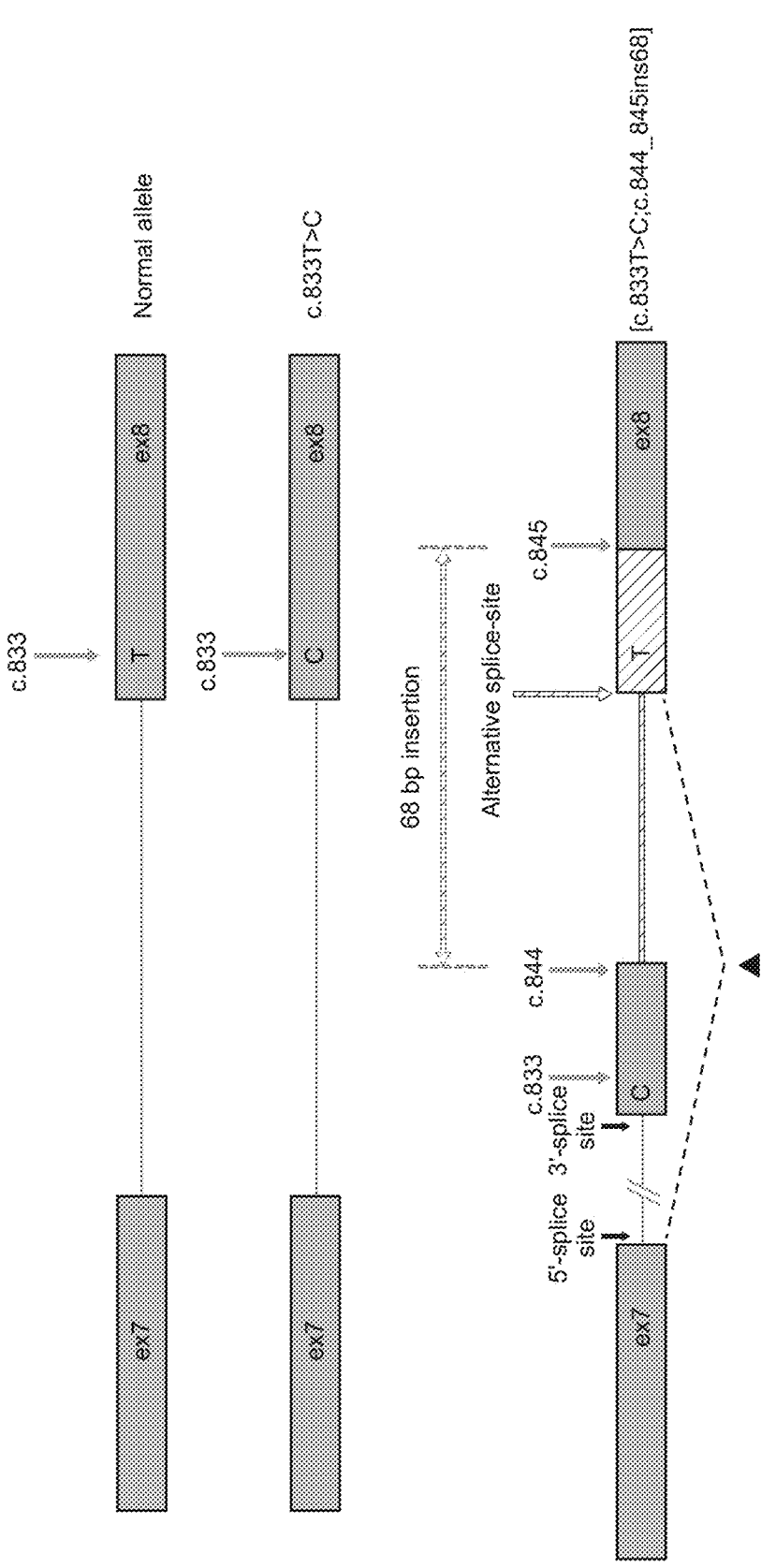

To enable the detection and phasing of targeted structural variants using short reads, a computational method that utilizes variant-specific customized reference sequences as scaffolds for read alignment was developed. This customization allows reads from different haplotypes to map correctly onto the corresponding custom scaffolds, resulting in improved genotype determination. Variant phasing may be further facilitated by the introduction of a marker in the scaffold sequence that enhances the efficient triaging of reads. These scaffolds can be constructed for any target region and incorporated into an existing variant analysis workflow without extensive algorithm development or increased analysis time.

In an embodiment, the custom scaffold approach focuses on detecting NGS variants in challenging regions, where standard reference-based alignment approaches (e.g., HG19, GRCh38) often lead to false positives or false negatives. For example, for genes with repetitive, homologous or pseudogene regions, the read alignment on standard reference genomes can have incorrect mapping or no mapping at all, resulting in false positives and false negatives in variant detection. As disclosed herein, custom scaffolds can be designed for each challenging variant and tailored for the proper separation of sequence reads by haplotypes ("haplotype separation"), greatly improving the efficiency of sequencing and detection sensitivity, specificity and phasing for challenging target variants. More specifically, disclosed herein is a specific improvement in the functionality of the sequencing system (e.g., NGS) itself, namely a reduction in improper separation of sequence reads by the sequencing system and improved sensitivity and specificity in variant calling and phasing by the variant identification and phasing system.

In certain embodiments, customized scaffolds may be constructed for each challenging variant. Such scaffolds may separate the reads with the variant from reads without the variant to improve detection sensitivity and specificity. Besides the variant of interest, these scaffolds may also include additional design parameters. As an example, for a cystathionine beta-synthase (CBS) complex variant with the 68 bp insertion, a base change may be introduced into the custom scaffold (inside the 68 bp insertion) to serve as the readout for the presence of the 68 bp insertion. As described in detail herein, having the base change in the scaffold also enables phasing between the 68 bp ins and a point mutation (c.833T>C) that may occur in the gene. This approach may be used for any variants that due to the structural nature of their sequence, may be difficult to detect and/or phase. For example, in addition to the examples disclosed herein, custom scaffolds have been developed for detecting a challenging 55 bp deletion in glucosylceramidase beta (GBA) where the resulting reads with the 55 bp deletion prefer to align to the GBAP1 pseudogene region.

Methods for Detection and Phasing of Complex Genetic Variants

Disclosed are techniques for detection and phasing of complex genetic variants. The techniques may be embodied in a variety of ways (e.g., a method, a system, non-transitory computer-readable medium storing code or instructions executable by one or more processors).

In an embodiment, disclosed is a method for detecting the presence or absence of a complex genetic variant in a sample comprising the steps of: (a) obtaining at least one mutant scaffold nucleotide sequence that comprises a sequence that includes mutations characteristic of the complex genetic variant; (b) obtaining a wild-type scaffold nucleotide sequence having a wild-type sequence; (c) generating an alignment of at least one sequence from the sample to the mutant scaffold and to the wild-type scaffold; and (d)

determining that the sample contains a mutation characteristic of the complex genetic variant based on alignment to the mutant scaffold and not the wild-type scaffold.

For example, as shown in FIG. 1, the method 100 may comprise the step 102 of determining the nature of the complex variant. This may be done by analyzing mutations that are known to be associated with the target of interest found in a database of sequences as described in detail for CBS herein. Next, the method may comprise the step 104 of obtaining a mutant scaffold sequence that incorporates at least one aspect (i.e., mutation) associated with the complex genetic variant (CGV). For example, the mutant scaffold may be constructed to incorporate a deletion and/or an insertion and/or a point mutation. The method may also include step 105 of obtaining additional mutant scaffolds that incorporate other mutations associated with the CGV. In some cases, at step 106, the mutant scaffold(s) may be constructed to include an additional variant sequence that can be used as a marker to indicate that a sequence aligned to the scaffold includes the mutation of interest. The method may further include step 107 of obtaining a scaffold that contains a defined wild-type sequence, and optionally, step 108 of obtaining a scaffold that includes a reference sequence.

To determine if a subject has the CGV, the method may include the step 109 of determining the DNA sequence for the subject at the target site associated with the CGV using e.g., methods, systems and computer-program products for sequencing, which are disclosed in detail herein. Or, the sequence data may be obtained from a database for characterization using the methods, systems and computer-program products disclosed herein. The method at step 110 may then generate alignments of the subject's nucleic acid sequence at the target of interest to the individual mutant, wild-type and optional reference scaffolds. In an embodiment, sequencing generates multiple sequence reads for the target of interest (e.g., NGS) such that multiple sequences are aligned to each of the scaffolds. The alignments may then be analyzed at step 112 to determine whether the subject contains a mutation associated with the CGV and optionally at step 114, to determine phasing of mutations (i.e., whether the mutations are on the same or different chromosome copies) associated with the CGV. The method may comprise the step 116 of reporting the results to the subject or a health care provider. In an embodiment, at least some of the method steps are controlled by a computing system, e.g., a computing system comprising a massively parallel sequencer.

In certain embodiments, the disclosed method may comprise determining that the complex variant sequence has two mutations and/or whether the two mutations are on the same chromosome (cis) or on different chromosomes (trans). By aligning sequences from the sample to the mutant and wild-type scaffolds it can be determined whether the mutation is heterozygous or homozygous in the sample. The method may be used for any complex variant. In an embodiment, the complex genetic variant is in the CBS gene. For example, in certain embodiments, the scaffolds distinguish (i) a sequence having a 68 bp insertion [844_845ins68] in cis with a c.833T>C mutation, from (ii) a sequence having the 68 bp insertion [844_845ins68] in trans with c.833T>C, from (iii) a sequence having the 68 bp insertion [844_845 ins68] without c.833T>C, or from (iv) a sequence having c.833T>C without the 68 bp insertion [844_845ins68]. Alternatively, the scaffolds may be used to distinguish other mutations in the CBS gene or any other gene in a similar manner.

FIGS. 2a and 2b depict a complex variant in the CBS gene. Specifically, FIG. 2a and FIG. 2b show the wild-type sequence (FIG. 2a) and the c.833T>C and the complex variant, c.[833T>C; 844_845ins68] for the CBS gene on chromosome 21 (FIG. 2b). The CBS gene encodes the enzyme cystathionine beta-synthase, and its deficiency causes homocystinuria. As shown in FIG. 2a, the sequence structures of the 68 bp insertion in cis with c.833T>C is equivalent to the c.832_833ins68 in ClinVar and gnomAD (public databases with free access to reports on genome sequencing data, and the relationships between human variations and phenotypes, with supporting evidence). In both panels, coding exon 8 is shaded with the c.833 wild-type base highlighted and the locations of the bases that differ between the wild-type and 68 bp insertion sequences enclosed by rectangular outline. The duplicated intronic sequence is underlined. In the lower panel, the 68 bp insertion sequences are shown in boxes with the relative locations of the c.833C variant in cis highlighted. Intronic sequence is in lowercase. FIG. 2b shows a schematic representation of the variant region depicting the exons with the locations of the c.833 base as a normal [T] or pathogenic [C] variant indicated. Also shown is the 68 bp insertion between the c.844 and c.845 bases as hatching. Dotted lines indicate the region that is excised due to alternative splicing.

Thus, as shown in FIGS. 2a and 2b, the c.844_845ins68 variant occurs near the 5'-end of coding exon 8 of the CBS gene and, with the exception of a few divergent bases, is a duplication of the last 52 bases of intron 7 and the first 16 bases of exon 8 (GRCh37/HG19 chr21:44483173-44483240). The inserted sequence includes a copy of the wild-type base, c.833T, as well as the 3'-splice site at the intron7-exon8 junction, the latter of which causes alternative splicing in the transcript. As a result, the c.833T wild-type base in the insertion is retained while the c.833T>C variant is excised if it is present in cis with the insertion (FIG. 2b). Consequently, when the c.833T>C variant occurs in cis with a 68 bp insertion, NM_000071.2:c.844_845ins68, it forms a benign complex variant, NM 000071.2:c.[833T>C; 844_845ins68]. Because clinical interpretation of c.833T>C depends on the presence of and phasing with c.844_845ins68, it is essential that both variants are correctly genotyped and phased in genetic testing.

Figure 3:
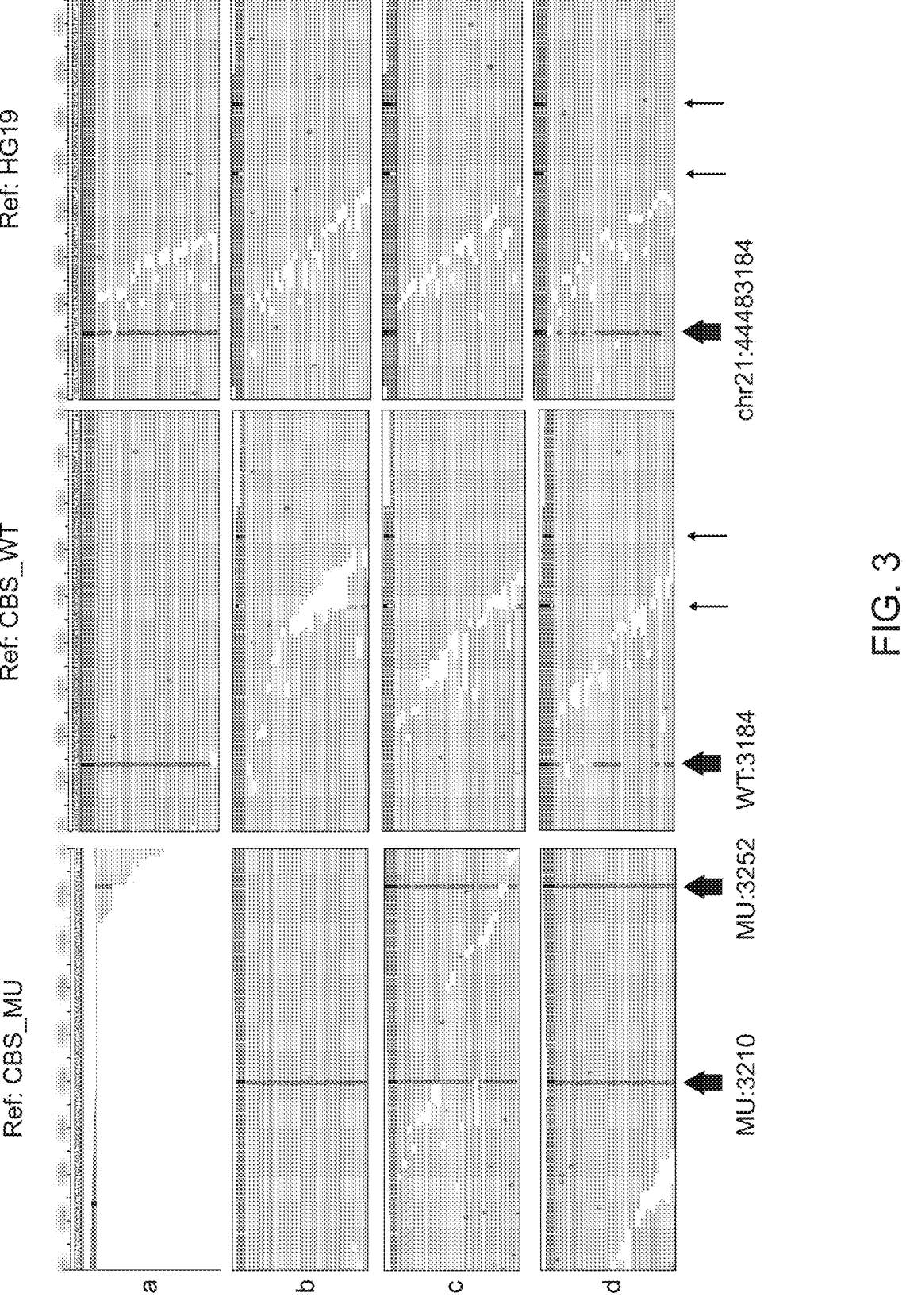
FIG. 3 shows alignment of simulated reads to the custom scaffolds and HG19 reference genome in accordance with an embodiment of the disclosure. Simulated read alignments to custom scaffolds CBS_MU (left panel) and CBS_WT (middle panel) and to HG19 reference genome (right panel) are shown for (a) c.833T>C, (b) c.844_845ins68, (c) c.833T>C in cis with c.844_845ins68 (i.e., c. [833T>C; 844_845ins68]) and (d) c.833T>C in trans with c. [833T>C; 844 845ins68].

In various embodiments, the scaffold is an in silico scaffold that is used to align high-throughput sequencing data. For example, FIG. 3 shows alignment of simulated reads to the custom scaffolds and the HG19 reference genome for the CBS complex genetic variant in accordance with an embodiment of the disclosure. Simulated read alignments to a custom mutant scaffold (CBS_MU) (left panel) and custom wild-type scaffold (CBS_WT) (middle panel) and to the HG19 reference genome (HG19) (right panel) are shown for (a) sequences with just a point mutation (c.833T>C), (b) sequences with just the 68 basepair (bp) insertion (c.844_845ins68, (c) sequences with the point mutation (c.833T>C) in cis with the 68 bp insertion (c.844_845ins68) (i.e., c.[833T>C; 844_845ins68]) and (d) sequences with the point mutation (c.833T>C) in trans with the 68 bp insertion (i.e., c.[833T>C; 844_845ins68]). Read alignments were visualized using the Integrative Genomics Viewer (IGV; Broad Institute, Cambridge, MA) with the DNA sequences shown above the per-base coverage tracks. In an embodiment, for the custom scaffolds alignments in b-d, some reads with the 68 bp insertion also align to Ref:CBS_WT due to high sequence homology; however, the soft-clipped ends are generally ignored by the variant caller. In an embodiment, with Ref:HG19, forced alignment and soft-clipping of all reads with the 68 bp insertion affects variant calling for the insertion and, when also present, the c.833T>C variant thus precludes detection of the complex variant. Arrows point to the informative bases that are used for variant calling on the scaffolds and HG19 reference. Two of the bases that differ between the 68 bp insertion and the HG19 reference sequence are shown with smaller arrows. A third divergent base at the very end of the insertion sequence is not visible in the alignments due to soft-clipping by the caller.

Thus, the CBS_WT scaffold represents the normal genotype (wild-type) and comprises 5,000 bp of the CBS gene region at chr21:44480001-44485000 based on GRCh37/HG19. The CBS_MU scaffold is the insertion genotype (mutant type) and comprises the same genomic region as the CBS_WT scaffold plus the common 68 bp insertion sequence. Due to the mismatch and gap penalty cost differences in the alignment algorithm, only reads that have the insertion will align to the CBS_MU scaffold. If the c.833T>C variant also occurs in the same paired-end reads as the 68 bp insertion, it would be detected as a base change at position 3252 in the CBS_MU scaffold (i.e., CBS_MU:3252A>G; FIG. 3c, Ref:CBS_MU). On the other hand, reads with just the c.833T>C variant will align to the CBS_WT scaffold, and this pathogenic variant can be identified as CBS_WT:3184A>G (FIG. 3a, Ref:CBS_WT).

In certain embodiments, the mutant scaffold comprises an additional genetic variation not found in either the complex variant sequence or the wild type sequence, wherein the additional genetic variation serves as a marker for the presence and/or phasing of the specific mutations comprising the complex genetic variant, as disclosed herein. For example, the CBS_MU scaffold has an additional G>C base change at scaffold position 3210 (designated CBS_MU:3210). Alteration of the "G" to a "C" base in the CBS_MU scaffold creates an expected mismatch that serves as a marker for a predetermined variant call to easily identify reads that have the 68 bp insertion (FIG. 2b, Ref:CBS_MU).

Thus in an embodiment, reads with just the c.833T>C variant align only to the CBS_WT scaffold (FIG. 3a, Ref: CBS_WT compared to Ref:CBS_MU). Reads with the c.844_845 ins68 variant preferentially align to the CBS_MU scaffold (FIG. 3b-d, Ref:CBS_MU) and are identified by the G>C readout at CBS_MU:3210, whereas co-occurrence of a base change at CBS_MU:3252A>G, also at 100% VAF, indicates that the 68 bp insertion is in cis with c.833T>C (FIG. 2c, Ref:CBS_MU). Because of high homology between the insertion and reference sequences, a fraction of reads with the c.844_845 ins68 sequence may also align to the CBS_WT scaffold due to soft-clipping of the unaligned read ends.

In an embodiment, the mutant scaffold is also used to determine the genotype of a sample with two copies of c.844_845 ins68, one that is in cis with c.833T>C and the other on the opposite allele. In this case, base changes at CBS_MU:3210G>C and CBS_MU:3252A>G at 100% and 50%, respectively, can identify the compound heterozygosity. Alternatively, if c.833T>C occurs in trans to c.[833T>C; 844_845ins68], read alignments to both the CBS_MU and CBS_WT scaffolds would be required using CBS_WT: 3184A>G, CBS_MU:3210G>C and CBS_MU:3252 A>G at ~60%, 100% and 100%, respectively, for detection, where the decrease in VAF for CBS_WT:3184 A>G from 100% to ~60% is expected due to the presence of c.833T>C on both alleles.

A variety of high-throughput sequencing platforms may be used to align the sequence data used for alignment. In an embodiment, the sequencing is next-generation sequencing (NGS) and performed with a massively parallel sequencer.

Systems for Detection and Phasing of Complex Genetic Variants

Figure 4:
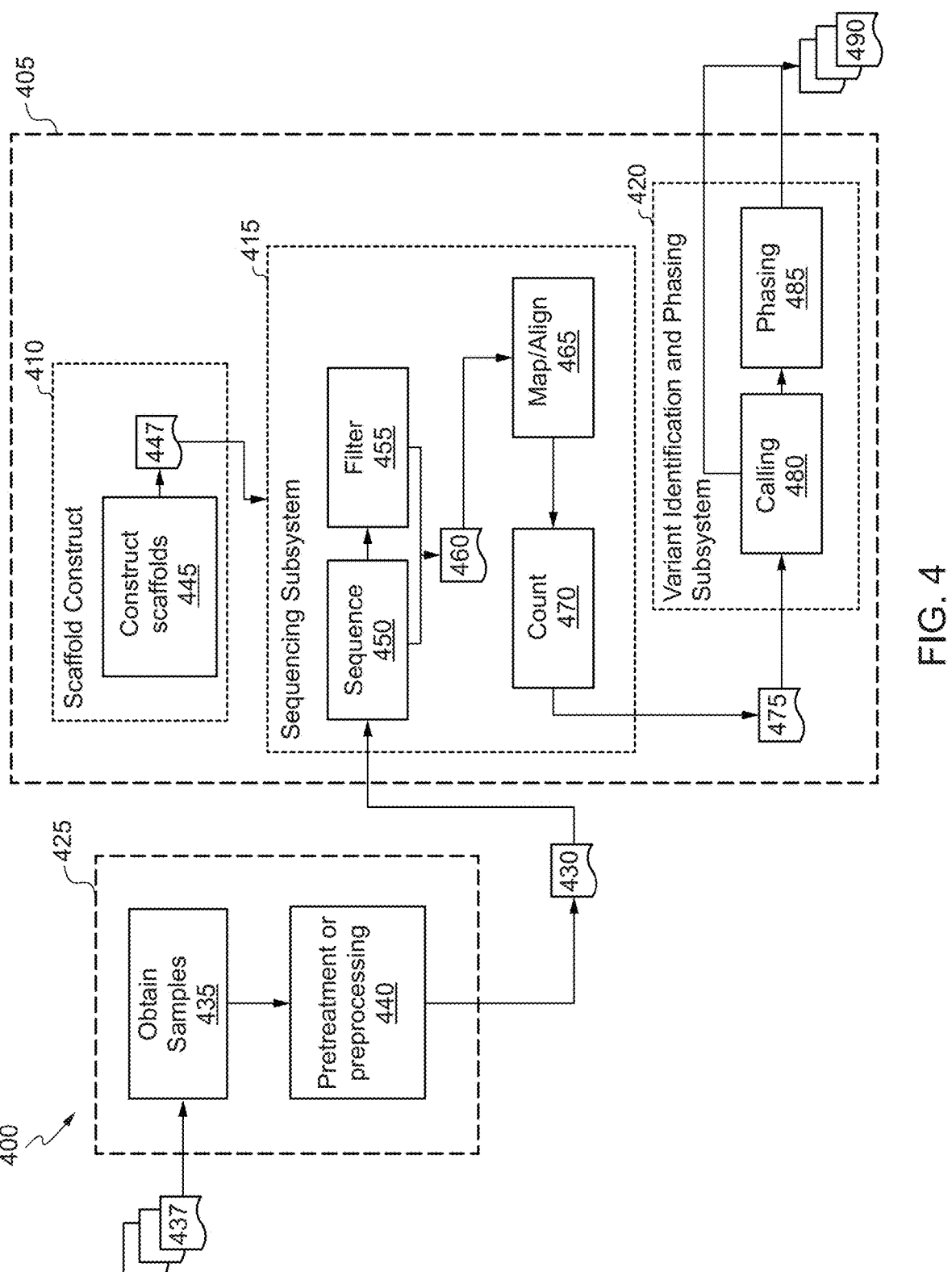
FIG. 4 shows a block diagram of a genomic variant calling platform in accordance with an embodiment of the disclosure.

One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines. FIG. 4 shows a block diagram of a genomic variant calling platform 400 for sequence acquisition and complex genetic variant identification and phasing in accordance with an embodiment of the disclosure, and illustrates modules, engines, or components (e.g., program, code, or instructions) executable by one or more processors that may be used to implement the various subsystems of an analyzer system 405 according to various embodiments. The modules, engines, or components may be stored on a non-transitory computer medium. As needed, one or more of the modules, engines, or components may be loaded into system memory (e.g., RAM) and executed by one or more processors of the analyzer system 405. In the example depicted in FIG. 4, modules, engines, or components are shown implementing a scaffold construct subsystem 410, a sequencing subsystem 415, and a variant identification and phasing subsystem 420.

FIG. 4 also illustrates a wet lab subsystem 425 including a laboratory where specimens, chemicals, drugs, or other material are tested and analyzed requiring reagents and specialized lab equipment for processing specimens and nucleic acid. The genomic variant calling platform 400 includes obtaining nucleic acid or a nucleic acid mixture 430 at block 435 within the wet lab subsystem 425. The nucleic acid 430 may be isolated from any type of suitable biological specimen or sample 437 (e.g., a test sample). A sample or test sample can be any specimen that is isolated or obtained from a subject or part thereof (e.g., a human subject, a pregnant female, a cancer patient, a fetus, a tumor, or the like). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants, normal cells, abnormal cells (e.g., cancer cells)) or parts thereof (e.g., mitochondrial, nucleus, extracts, or the like). In certain instances, the nucleic acid 430 includes one or more variants. As used herein, the term "variant" or "sequence variant" refers to a nucleic acid sequence that is different from a reference sequence and/or scaffold sequence. Typical nucleic acid sequence variants include without limitation single nucleotide polymorphism (SNP), short deletion and insertion polymorphisms (Indel), copy number variation (CNV), microsatellite markers or short tandem repeats, and structural variation.

At block 440 within the wet lab subsystem 425, the nucleic acid 430 is pretreated or preprocessed. Methods of pretreatment or preprocessing may include, but are not limited to, filtration, precipitation, enrichment, dilution, distillation, mixing, centrifugation, freezing, lyophilization, concentration, amplification, nucleic acid fragmentation, inactivation of interfering components, the addition of reagents, lysing, library preparation, and the like.

In some instances, the nucleic acid 430 is fragmented by cleaving or shearing. For example, a nucleic acid molecule, such as a nucleic acid template gene molecule or amplified product thereof, may be severed into two (or more) smaller nucleic acid molecules. The shearing or cleavage can be sequence specific, base specific, or nonspecific, and can be accomplished by any of a variety of methods, reagents or conditions, including, for example, chemical, enzymatic, physical shearing (e.g., physical fragmentation). Sheared or cleaved nucleic acids can be generated by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), the like or combinations thereof.

In some instances, the nucleic acid 430 is amplified. For example, the nucleic acid (e.g., a target nucleic acid) in a sample may be subjected to a process that linearly or exponentially generates amplicon nucleic acids having the same or substantially the same nucleotide sequence as the target nucleic acid, or part thereof. In certain embodiments, the amplification of the nucleic acid 430 comprises a polymerase chain reaction (PCR).

In some instances, a nucleic acid library is generated based on the nucleic acid 430. The nucleic acid library may comprise a plurality of polynucleotide molecules (e.g., a sample of nucleic acids) that are prepared, assembled and/or modified for a specific process, non-limiting examples of which include immobilization on a solid phase (e.g., a solid support, a flow cell, a bead), enrichment, amplification, cloning, detection and/or for nucleic acid sequencing. The nucleic acid library may be prepared by a targeted or a non-targeted preparation process.

At block 445 within the scaffold construct subsystem 410, one or more scaffolds 447 are constructed for facilitating improvement in the detection and phasing efficiency, sensitivity, and specificity for challenging target variants. As used herein, "scaffolds" are sequence assemblies constructed in silico to which new reads may be aligned. The sequence assemblies may comprise a series of contigs that are in the right orientation and order but not necessarily connected in one continuous stretch of sequence. A contig (from contiguous) is a set of overlapping nucleotide segments that together represent a consensus region of a nucleotide sequence. In various instances, one or more scaffolds 447 are constructed in silico for a target region of a chromosome or genome such as the CBS gene region. The target region may be selected as a region known to have a complex genetic variant. As used herein, a "complex genetic variant" is a structural variant (i.e., mutations in the genome of size at least fifty nucleotides) or a variant residing in repetitive or highly homologous sequences.

In some instances, a mutant scaffold nucleotide sequence is constructed for the target region that comprises a sequence that includes mutations characteristic of the complex genetic variant, and a wild-type scaffold nucleotide sequence is constructed for the target region having a wild-type sequence. The mutant scaffold(s) and the wild-type scaffold allow for discriminating between sequence reads that have a complex genetic variant versus sequence reads that do not have the complex genetic variant. The wild-type scaffold is constructed to encompass base pairs of the normal genotype for the target region. In certain instances, the wild-type scaffold is constructed based off a reference genome for a genome comprising the target region. The mutant scaffold is constructed to encompass base pairs of the abnormal geno-type for the target region including the mutations (i.e., base pairs for the wild type sequence and the complex genetic variant sequence). In some instances, the mutant scaffold is further constructed to include an additional genetic variation not found in either the complex genetic variant sequence or the wild type sequence. The additional genetic variation may serve as a marker for the presence and/or phasing of the specific mutations comprising the complex genetic variant. For example, a first scaffold, CBS_WT, may be constructed identical to the hg19 reference region chr21:44,480,001-44,485,000. The second scaffold, CBS_MU, may also be constructed from the same region, but include the common 68 bp insertion plus an introduced G>C base change within the 68 bp insertion that serves as a marker to detect the insertion.

At block 450 within the sequencing subsystem 415, the nucleic acid 430 (optionally preprocessed or pretreated) is sequenced. Nucleic acid sequencing generally produces a collection of sequence reads. As used herein, "reads" (e.g., "a read," "a sequence read") are short nucleotide sequences produced by any sequencing process described herein or known in the art. Reads can be generated from one end of nucleic acid fragments ("single-end reads"), and sometimes are generated from both ends of nucleic acid fragments (e.g., paired-end reads, double-end reads). The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more. Any suitable method of sequencing nucleic acids can be used, non-limiting examples of which include next gen-eration (e.g., 2nd and 3rd generation) sequencing techniques capable of sequencing DNA in a massively parallel fashion (e.g., with a massively parallel sequencer). In some embodi-ments, the next generation sequencing methods utilize a targeted approach, where specific chromosomes, genes or regions of interest are sequenced. For example, nucleic acid from the sample may be sequenced for a target region (e.g., a target region of CBS gene or the CBS gene itself). In certain embodiments, a non-targeted approach is used where most or all nucleic acids in a sample are sequenced, ampli-fied and/or captured randomly.

At block 455 within the sequencing subsystem 415, the sequence reads may be filtered. In some embodiments, certain sequence reads are filtered out (i.e., excluded from sequence read analysis for determining the presence or absence of a genetic alteration such as a complex genetic variant sequence). Reads that may be filtered out include, for example, discordant reads, ambiguous reads, off-target reads, reads having a single molecule barcode (SMB) sequence with one or more undetermined base calls, reads having a low quality sample index, and reads having a low quality barcode (e.g., single molecule barcode). Low quality sequences (e.g., barcode, index) may be identified according to base quality scores for one or more nucleotide positions in a sequence. A base quality score, or quality score, is a prediction of the probability of an error in base calling.

Quality scores may be generated by a quality table that uses a set of quality predictor values, and can depend on certain characteristics of the sequencing platform used for generat-ing sequence reads. Generally, a high quality score indicates a base call is more reliable and less likely is an incorrect base call. For example, for base calls with a quality score of 40, one incorrect base call in 10,000 base calls may be predicted, or for base calls with a quality score of 30, one incorrect base call in 1,000 base calls may be predicted, or for base calls with a quality score of 10, one incorrect base call in 10 base calls may be predicted.

The sequence reads (optionally filtered) and optional quality scores are output as raw sequencing data 460. In some instances, the raw sequencing data 460 is output in a standardized file format such as a FASTQ file for further processing. In other instances, the raw sequencing data 460 is output in a base format such as binary base call (BCL) format and converted with demultiplexing to a standardized file format such as a FASTQ for further processing. FASTQ is a text-based sequencing data file format that stores both raw sequence data and quality scores.

At block 465 within the sequencing subsystem 415, the sequence reads of the raw sequencing data 460 are mapped and the number of reads mapping to a specified nucleic acid region (e.g., a chromosome or portion thereof such as a target region) are referred to as counts. Mapping nucleotide sequence reads (i.e., sequence information from a fragment whose physical genomic position is unknown) comprises alignment of the obtained sequence reads with a matching sequence (e.g., genomic portions or enriched portions (e.g., target enrichment probes)) in a reference genome or the one or more scaffolds 447. In such alignments, the sequence reads are aligned to a reference sequence or the one or more scaffolds 447, and those sequence reads that aligned are designated as being "mapped," as "a mapped sequence read" or as "a mapped read." In certain instances, the sequence reads are mapped to matching sequences that include the complex genetic variant sequence in the mutant scaffold, and the sequence reads are mapped to matching sequences that include the wild-type sequence in the wild-type scaffold.

Aligned or alignment refers to two or more nucleic acid sequences (e.g., a sequence read and a mutant scaffold) that can be identified as a match (e.g., 100% identity) or partial match. Alignments are done by a computer (e.g., a software, program, module, or algorithm), non-limiting examples of which include the Efficient Local Alignment of Nucleotide Data (ELAND) computer program distributed as part of the Illumina Genomics Analysis pipeline. In some instances, alignment of a sequence read can be a 100% sequence match. In other instances, an alignment is less than a 100% sequence match (i.e., non-perfect match, partial match, partial alignment). In certain instances, the alignment algo-rithm is parameterized to include a mismatch and gap penalty cost difference such that only reads that have a variant or complex genetic variant will align to the mutant scaffold. A mapped sequence read may be referred to as a "hit" or "count." In some embodiments, mapped sequence reads are grouped together (i.e., partitioned) according to various parameters and assigned to particular genomic por-tions or scaffolds 447. The alignment of the sequence reads of the raw sequencing data 460 with the one or more scaffolds 447 results in a specific improvement in the functionality of the sequencing system (e.g., NGS) itself, namely a reduction in improper separation of sequence reads by the sequencing system and improved sensitivity and specificity in variant calling and phasing by the variant identification and phasing system. More specifically, the mismatch and gap penalty cost forces the reads to map to the location with the lowest cost (zero or minimal mismatch or gap). As a result, reads from the wild-type always map to the wild-type scaffold, while reads with the mutant always map to the mutant scaffold. This also applies to haplotypes if the read length is long enough to cover both variants belonging to the same haplotype ("phasing").

At block 470 within the sequencing subsystem 415, sequence reads that are mapped or partitioned based on a selected feature or variable can be quantified to determine the amount or number of reads that are mapped to one or more portions (e.g., portion of a reference genome or the one or more scaffolds 447). In some embodiments the quantity of sequence reads that are mapped to a portion or segment is referred to as a count or read density. In certain embodiments, the sequence reads mapped to the sequences that include the complex genetic variant sequence are counted and the sequence reads mapped to the sequences that include the wild-type sequence are counted. The counting generates a quantification of the sequence reads mapped to the sequences that include the complex genetic variant sequence and a quantification of the sequence reads mapped to the sequences that include the wild-type sequence.

A count can be determined by a suitable method, operation or mathematical process. The count sometimes is the direct sum of all sequence reads mapped to a genomic portion or a group of genomic portions corresponding to a segment, a group of portions corresponding to a sub-region of a genome (e.g., copy number variation region, copy number alteration region, copy number duplication region, copy number deletion region, microduplication region, microdeletion region, chromosome region, autosome region, sex chromosome region) and/or sometimes is a group of portions corresponding to a genome. A read quantification sometimes is a ratio, and sometimes is a ratio of a quantification for portion(s) in region a to a quantification for portion(s) in region b. Region a sometimes is one portion (e.g., the wild-type scaffold), segment region, copy number variation region, copy number alteration region, copy number duplication region, copy number deletion region, microduplication region, microdeletion region, chromosome region, autosome region and/or sex chromosome region. Region b independently sometimes is one portion (e.g., the mutant scaffold), segment region, copy number variation region, copy number alteration region, copy number duplication region, copy number deletion region, microduplication region, microdeletion region, chromosome region, autosome region, sex chromosome region, a region including all autosomes, a region including sex chromosomes and/or a region including all chromosomes.

The alignments may be converted to a standardized format such as BAM file, sorted and indexed using a sorting tool, and output as raw mapping data 475. The alignments include read name, read sequence, read quality, alignment information, custom tags, and count or quantification information. The read name includes the chromosome, start coordinate, alignment quality, and the match descriptor string. In some instances, the mapping and alignment processes performed in blocks 465 and 470 may further comprise merging lanes (e.g., merging sequence alignments from multiple samples), marking duplicates (e.g., identify reads that are likely artificial duplicates originated during sequencing workflow), detect and correct systematic errors in the base quality scores (e.g., base quality score recalibration), and/or check the quality of the mapping and alignments (e.g., examine sequencing alignment data in raw mapping data 475 according to the features of the mapped reads and provide an overall view of the data that helps to detect biases in the sequencing and/or mapping of the data).

At block 480 and optionally block 485 within the variant identification and phasing subsystem 420, the raw mapping data 475 is analyzed, using techniques described herein, to: (i) detect variants including complex genetic variants within the sequence reads, and optionally (ii) assign detected variants to chromosomes of origins (i.e., phasing). A variant call is a conclusion that there is a nucleotide difference versus a reference (e.g., the reference genome and/or the one or more scaffolds 447) at a given position in an individual genome or transcriptome. The variant call may be accompanied by an estimate of variant frequency and a measure of confidence for the variant call. The variant calling may include identifying where the aligned reads differ from the reference genome and/or the one or more scaffolds 447 (i.e., counting read coverage of positions within the reads sequences and detecting variants including complex genetic variants based on position-based counting information), and outputting the identified differences or variants as a portion of the variant identification and optional phasing data 490 in a standardized file format such as a variant call format (VCF). Predetermined thresholds may be used for variant filtering and detection. For example, one criterion may include requesting all reported variants that have at least 5 alternative allele depth and more than 1% allele fraction. However, each locus in the genome may have different characteristics in terms of sequence context, mappability, background noise level, etc. A position-specific threshold or position-specific model may be used to distinguish signal or true variant from background noise.

In some instances, the variant calling may include determining whether the sample contains a mutation characteristic of the complex genetic variant based on alignment of one or more sequences from the sample to the mutant scaffold and not alignment (absence of alignment) of one or more sequences from the sample to the wild-type scaffold. This determination may be made based on the quantification of the sequence reads mapped to the sequences that include the complex genetic variant sequence versus the quantification of the sequence reads mapped to the sequences that include the wild-type sequence. In certain instances, a determination is made that the sample contains the mutation characteristic of the complex genetic variant based on the quantification of the sequence reads mapped to the sequences that include the complex genetic variant sequence versus the quantification of the sequence reads mapped to the sequences that include the wild-type sequence. For example, if the quantification of the sequence reads mapped to the sequences that include the complex genetic variant sequence are greater that a set threshold amount then a determination may be made that the sample contains the mutation characteristic of the complex genetic variant. Alternatively, if the quantification of the sequence reads mapped to the sequences that include the complex genetic variant sequence are greater that a set threshold amount and the quantification of the sequence reads mapped to the sequences that include the wild-type sequence are less that a set threshold amount then a determination may be made that the sample contains the mutation characteristic of the complex genetic variant.

The variant calling may further include phasing which includes determining whether the mutation is heterozygous or homozygous in the sample. For example, determining whether two mutations are on the same chromosome (cis) or on different chromosomes (trans). In some instances, the variant calling may further include determining that the read sequences have two or more mutations. The mutant scaffold and the wild-type scaffold are capable of discriminating (i) a sequence having a complex variant sequence in cis with a pathogenic mutation, from (ii) a sequence having a complex variant sequence in trans with a pathogenic mutation, from (iii) a sequence having a complex variant sequence without a pathogenic mutation, or from (iv) a sequence having a pathogenic mutation without the complex variant sequence. The phasing information may be output as a portion of the variant identification and phasing data 490 in a standardized file format. Accordingly, if a pathogenic variant such as the c.833T>C variant also occurs in the same paired-end reads as the complex genetic variant, the pathogenic variant would be detected as a base change in the mutant scaffold. On the other hand, reads with just the pathogenic variant will align to the wild-type scaffold, and the pathogenic variant will be identified.

To facilitate efficient variant calling and phasing, the mutant scaffold may be constructed with an additional artificial genetic variation (e.g., a base change at a scaffold position). The additional artificial genetic variation is not found in either the complex variant sequence or the wild type sequence. The additional artificial genetic variation in the mutant scaffold creates an expected mismatch that serves as a marker for a predetermined variant call to easily identify reads that have the complex genetic variant (e.g., for the presence and/or phasing of the mutation characteristic of the complex genetic variant). The mapping the sequence reads to matching sequences that include the complex genetic variant sequence in the mutant scaffold may further comprise identifying an expected mismatch between the sequence reads and the matching sequences that include the complex genetic variant sequence based on the additional artificial genetic variation. The counting the sequence reads mapped to the sequences that include the complex genetic variant sequence may further include counting the sequence reads mapped to the sequences that include the complex genetic variant sequence and the additional artificial genetic variation.

A result 490 that the sample contains the presence or absence of the complex genetic variant is output or provided based on the determination of whether the sample contains the mutation. For example, the presence or absence of the complex genetic variant may be locally presented or transmitted to another device. The presence or absence of the complex genetic variant may be output along with an identifier of a subject (e.g., the subject associated with the sample). In some instances, the presence or absence of the complex genetic variant is output to an end user or storage device. In some instances, the result that the sample contains the presence or absence of the complex genetic variant is output with notation concerning the two mutations being on the same chromosome (cis) or on different chromosomes (trans) based on the determination of whether the sample contains the mutation characteristic of the complex genetic variant and whether the two mutations are on the same chromosome (cis) or on different chromosomes (trans). Thus, the determination of heterozygous or homozygous could be used to impact treatment decisions and therapeutic options and protocols. Optionally, a treatment is administered to a subject associated with the sample in accordance with the presence of the complex genetic variant in the sample. Alternatively, a computer-implement method, system, or computer program product initiates treatment (e.g., provides a result with a recommendation to a healthcare worker to start a given treatment, provides a result that automatically triggers a treatment action, provides a result that causes a health care worker to take treatment action based on the result, and the like) to a subject associated with the sample in accordance with the presence of the complex genetic variant in the sample. In some instances, the treatment is a therapeutic agent or a prescribed dietary change. For example, in the instance that the complex genetic variant is in the target region of the CBS gene, the therapeutic agent may be vitamin B6 or the dietary change may be a low-methionine diet.

Figure 5:
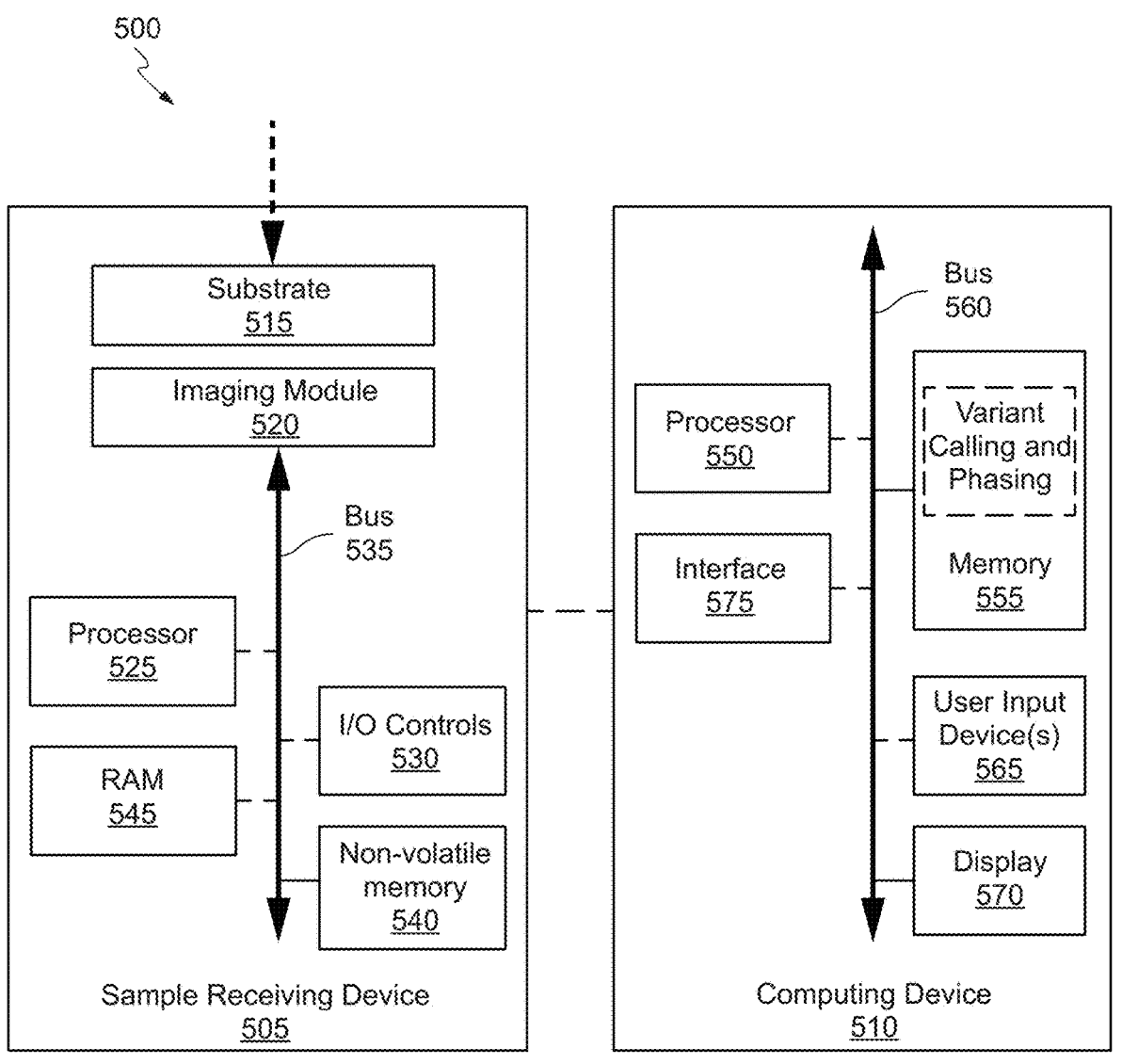
FIG. 5 shows a computer-implemented analysis system for complex genetic variant identification and phasing in accordance with an embodiment of the disclosure.

FIG. 5 is a schematic diagram of an analyzer system 500 (e.g., the analyzer system 405 described with respect to FIG. 4) that may be used in conjunction with the disclosed embodiments for acquiring sequencing data that is used to identify and/or validate sequence variant calls and phasing as disclosed herein. The analyzer system 500 may be implemented according to any sequencing technique, such as those incorporating sequencing-by-synthesis techniques, ligation techniques, nanopore sequencing, fluorescent in situ sequencing (FISSEQ), and Massively Parallel Signature Sequencing (MPSS). In particular embodiments, the analyzer system 500 may be configured to operate using a CMOS sensor with nanowells fabricated over photodiodes such that DNA deposition is aligned one-to-one with each photodiode. The analyzer system 500 may be "one-channel" detection device, in which only two of four nucleotides are labeled and detectable for any given image. For example, thymine may have a permanent fluorescent label, while adenine uses the same fluorescent label in a detachable form. Guanine may be permanently dark, and cytosine may be initially dark but capable of having a label added during the cycle. Accordingly, each cycle may involve an initial image and a second image in which dye is cleaved from any adenines and added to any cytosines such that only thymine and adenine are detectable in the initial image but only thymine and cytosine are detectable in the second image. Any base that is dark through both images in guanine and any base that is detectable through both images is thymine. A base that is detectable in the first image but not the second is adenine, and a base that is not detectable in the first image but detectable in the second image is cytosine. By combining the information from the initial image and the second image, all four bases are able to be discriminated using one channel.

The analyzer system 500 may include a separate sample processing device 505 and a computing device 510. However, these may be implemented as a single device. Further, the computing device 510 may be local to or networked with the sample processing device 505. In the depicted embodiment, the sample may be loaded into the computing device 510 on a sample substrate 515, e.g., a flow cell or slide, that is imaged to generate sequence data. For example, reagents that interact with the biological sample fluoresce at particular wavelengths in response to an excitation beam generated by an imaging module 520 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics. This retrobeam may generally be directed toward detection optics of the imaging module 520.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, any similar technology, or any combination thereof (e.g., TDI mode detection can be coupled with line scanning).

The imaging module 520 may be under processor control, e.g., via a processor 525, and the sample receiving device 505 may further include I/O controls 530, an internal bus 535, non-volatile memory 540, RAM 545 and any other memory structure such that the memory is capable of storing executable instructions sequence processing as described herein. The computing device 510 may include a processor 550 which is in communication with the memory 555 and other components of the computing device 510 using one or more communications buses 560. The processor 550 is configured to execute processor-executable instructions stored in the memory 555 to operate on the genomic sequence data as provided herein. In particular embodiments, based on the image data acquired by the imaging module 520, the analyzer system 500 may be configured to generate sequencing data that includes base calls for each base of a sequence read. Further, based on the image data, the individual reads may be mapped or aligned to a reference genome and/or one or more scaffolds. The processor 550 may also be programmed to perform downstream analysis such as variant calling and phasing on the aligned sequence reads. The processor 550 may be configured to operate on sequence data in the form of a standardized format such as a BAM file and to output the variant calls and phasing in various standardized formats, such as in a VCF or GVCF files.

The computing device 510, in this example, also includes one or more user input devices 565, such as a keyboard, mouse, touchscreen, microphone, etc., to accept user input. The computing device 510 also includes a display 570 to provide visual output to a user such as a user interface. The computing device 510 also includes a communications interface 575. In some examples, the communications interface 575 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

EXAMPLES

The custom scaffolds approach was assessed for the detection of a clinically significant, complex variant of the CBS gene. The CBS gene encodes the enzyme cystathionine beta-synthase, and its deficiency causes homocystinuria (OMIM 236200). Carrier testing panels may assess pathogenic CBS variants, including the single nucleotide variant NM_000071.2:c.833T>C (r55742905, NP_000062.1: p.Ile278Thr, HG19 chr21:44483184A>G). This variant has a reported population carrier frequency that ranges from 0.02% (1000 Genomes Project) to 0.15% (Genome Aggregation Database or gnomAD; converted from a chromosome-based population frequency of p=0.08% using the formula, 2*p*[1-p], and assuming Hardy-Weinberg equilibrium). The c.833T>C variant often occurs in cis with a 68 bp insertion, NM_000071.2:c.844_845ins68, to form a benign complex variant, NM_000071.2:c.[833T>C; 844_845ins68]. The population carrier frequency for c.[833T>C; 844_845ins68] varies greatly among different ethnic groups, ranging from 40-50% in Africans and Northern Europeans to 2.5% in East Asians, and <1% in Native American populations. To date, c.844_845ins68 has been reported to segregate in cis only with the c.833T>C mutation; however, several other scenarios are also plausible, including c.[833T>C; 844_845ins68] in trans with c.833T>C, a complex variant which may even attenuate disease severity. Because clinical interpretation of c.833T>C depends on the presence of and phasing with c.844_845ins68, it is essential that both variants are correctly genotyped and phased in genetic testing.

Disclosed is the design and construction of variant-specific custom scaffolds that can correctly differentiate all possible genotype and phasing permutations of the CBS variants, c.833T>C and c.844_845ins68. The usefulness of the approach in clinical testing is demonstrated by applying the method to the detection of the c.833T>C variant, either alone or as a complex variant c.[833T>C; 844_845ins68], in more than 60,000 patient specimens and two 1000 Genomes Project cell line trios. When compared with the conventional method of using one primary sequence as reference for alignment, the customized scaffolds method circumvented issues with mapping bias, and also yielded important phasing information. The disclosed methods and systems significantly improved assay sensitivity and specificity, especially for complex variants that may be underestimated in population datasets.

Custom Scaffolds Composition and Variant Call Analysis

To define the 68 bp insertion sequence for use in our custom scaffolds approach, the gnomAD and ClinVar databases were searched. It was and found that there were two descriptions for the variant: NM_000071.2:c.844_845ins68 (ClinVar Variation ID 212823) and NM_000071.2: c.832_833ins68 (ClinVar Variation ID 226482). These descriptions differed in their insertion sites and sequences, and when c.833T>C was present in cis, its location could be assigned as either part of the insertion sequence (i.e., c.832_833ins68) or separate from it (i.e., [c.833T>C; 844_845ins68]). Upon further scrutiny, it was concluded that both descriptions were equivalent since the sequences for the 68 bp insertion and wild-type genome are identical at the sites in which the insertions occur in the exon (FIG. 2a). In order to distinguish c.833T>C from the insertion sequence in the analysis as well as for consistency, the 68 bp insertion is referred to as c.844_845 ins68 and the cis variant as c.[833T>C; 844_845ins68]. As discussed herein, the c.844_845 ins68 variant occurs near the 5'-end of coding exon 8 of the CBS gene and, with the exception of a few divergent bases, is a duplication of the last 52 bases of intron 7 and the first 16 bases of exon 8 (GRCh37/HG19 chr21: 44483173-44483240). The inserted sequence includes a copy of the wild-type base, c.833T, as well as the 3'-splice site at the intron7-exon8 junction, the latter of which causes alternative splicing in the transcript. As a result, the c.833T wild-type base in the insertion is retained while the c.833T>C variant is excised if it is present in cis with the insertion (FIG. 2*b*). It was also noted that two alternate alleles of the c.844_845 ins68 variant have been reported in gnomAD (v2.1.1). One allele differs by 3 bases from the GRCh37/HG19 reference genome (~96% identical; hereafter referred to as the common 68 bp insertion) and is more prevalent in the general population than the other, which has an additional divergent base (~94% identical with HG19) and is identified only in 16 individuals of African ethnicity in gnomAD (denoted hereafter as the rare 68 bp insertion). Nevertheless, with either allele sequence, the high similarity between the 68 bp insertion and the reference genome sequences (e.g., GRCh37/HG19 or GRCh38/HG38) causes forced alignment of reads having the c.[833T>C; 844_845ins68] complex variant to a standard genome assembly, thereby complicating detection of the insertion and/or the c.833T>C variant and potentially leading to a false call.

To address this challenge, two custom scaffolds (CBS_WT and CBS_MU) to discriminate reads with and Assessment of Customized Scaffolds Approach Using Simulated Reads To assess the custom scaffolds for read mapping specificity, simulated reads representing all possible genotype combinations were generated using the ART simulation tool kit. The variant calls that were tested as well as the corresponding variant allele frequencies (VAF) are compiled in Table 1, which also functions as the lookup table in the genotype calling process. Shown are the custom scaffold used and the percentage of reads that align to each scaffold for a given CBS genotype. Note that since the custom CBS_MU scaffold contains the 68 bp insertion sequence, any variant combination that includes c.844_845 ins68 on at least one allele will have a variant frequency of 100% at MU:3210C>G. Because a minority of reads with the 68 bp insertion will also align to the CBS_WT scaffold, a sample that is heterozygous for either c.844_845 ins68 or c.[833T>C; 844_845ins68] will have more reads mapping to this scaffold compared with one that is homozygous.

TABLE 1

| CBS Genotypes | Scaffold Alignment | | | Variant Allele Frequency (VAF) | | |
|---|---|---|---|---|---|---|
| | WT: 3184 A > G | MU: 3210 C > G | MU: 3252 A > G | WT: 3184 A > G | MU: 3210 C > G | MU: 3252 A > G |
| c.833T > C | Y | — | — | 50% (HET); 100% (HOM) | — | — |
| c.844_845ins68 | — | Y | — | — | 100% | — |
| c.[833T > C; 844_845ins68] | — | Y | Y | — | 100% | 100% |
| c.[833T > C] in trans with c.[844_845ins68] | Y | Y | — | ~60% | 100% | — |
| c.[833T > C] in trans with c.[833T > C; 844_845ins68] | Y | Y | Y | ~60% | 100% | 100% |
| c.[844_845ins68] in trans with c.[833T > C; 844_845ins68] | — | Y | Y | — | 100% | 50% | without the 68 bp insertion were constructed (FIG. 3). The CBS_WT scaffold represents the normal genotype and encompasses 5,000 bp of the CBS gene region at chr21: 44480001-44485000 based on GRCh37/HG19. The CBS_MU scaffold is the insertion genotype and consists of the same genomic region as the CBS_WT scaffold plus the common 68 bp insertion sequence. Due to the mismatch and gap penalty cost differences in the alignment algorithm, only reads that have the insertion will align to the CBS_MU scaffold. To facilitate efficient variant calling and phasing, the CBS_MU scaffold was also constructed with an additional G>C base change at scaffold position 3210 (designated CBS_MU:3210). The wild-type base at this position is highly conserved among primates and has no known polymorphisms or pathogenic variants according to the 1000 Genomes Project and dbSNP150 databases. Alteration of the "G" to a "C" base in the CBS_MU scaffold creates an expected mismatch that serves as a marker for a predetermined variant call to easily identify reads that have the 68 bp insertion (FIG. 2*b*, Ref:CBS_MU). If the c.833T>C variant also occurs in the same paired-end reads as the 68 bp insertion, it would be detected as a base change at position 3252 in the CBS_MU scaffold (i.e., CBS_MU:3252A>G; FIG. 3*c*, Ref:CBS_MU). On the other hand, reads with just the c.833T>C variant will align to the CBS_WT scaffold, and this pathogenic variant will be identified as CBS_WT: 3184A>G (FIG. 3*a*, Ref:CBS_WT).

As expected, reads with just the c.833T>C variant aligned only to the CBS_WT scaffold (FIG. 3*a*, Ref:CBS_WT compared to Ref:CBS_MU). Reads with the c.844_845 ins68 variant preferentially aligned to the CBS_MU scaffold (FIG. 3*b-d*, Ref:CBS_MU) and were easily identified by the G>C readout at CBS_MU:3210 at 100% VAF, whereas co-occurrence of a base change at CBS_MU:3252A>G, also at 100% VAF, indicated that the 68 bp insertion was in cis with c.833T>C (FIG. 3*c*, Ref:CBS_MU). Because of high homology between the insertion and reference sequences, a fraction of reads with the c.844_845 ins68 sequence also aligned to the CBS_WT scaffold due to soft-clipping of the unaligned read ends. The resulting increase in coverage depth may suggest that there is a structural variant; however, the 68 bp insertion sequence is not identified as such since the variant caller ignores the soft-clipped bases (FIG. 3*b*, Ref:CBS_WT). The Ref:CBS_MU scaffold was also used to determine the genotype of a sample with two copies of c.844_845 ins68, one that is in cis with c.833T>C and the other on the opposite allele (Table 1, last row). In this case, base changes at CBS_MU:3210G>C and CBS_MU: 3252A>G at 100% and 50% VAF, respectively, would identify the compound heterozygosity. Alternatively, if c.833T>C occurs in trans to c.[833T>C; 844_845ins68], read alignments to both the CBS_MU and CBS_WT scaffolds would be required using CBS_WT:3184A>G, CBS_MU:3210G>C and CBS_MU:3252 A>G at ~60%, 100% and 100% VAF, respectively, for detection (Table 1, penultimate row; FIG. 3*d*). The decrease in VAF for CBS_WT:3184 A>G from 100% to ~60% is expected due to the presence of c.833T>C on both alleles.

Compared to the custom scaffolds approach, alignment to the HG19 reference genome posed a challenge for detection and phasing of the CBS variants (FIG. 3*b-d*, Ref:HG19). Since the 68 bp insertion is essentially a duplication of the wild-type sequence, all reads with this variant, whether alone or in combination with c.833T>C, were forced to align to the HG19 reference genome by soft-clipping the unaligned read ends at the left and right breakpoints. The resulting increase in read coverage may indicate an insertion (FIG. 3*b-d*, Ref:HG19), but because of the additional presence of the wild-type c.833T base in the insertion sequence, the c.833T>C allele frequency at chr21:44483184 could fall below the variant calling threshold, thereby impacting detection of the c.833T>C variant (FIG. 3*c*, Ref:HG19). In contrast, reads with only the pathogenic variant c.833T>C readily aligned with the HG19 reference sequence and the variant was easily detected at chr21:44483184 (FIG. 3*a*, Ref:HG19). Alignment of reads with the variant in trans with the c.[833T>C; 844_845ins68] complex variant had a similar profile to that of c.833T>C by itself but with a lower allele frequency for the mutant base at chr21:44483184 (FIG. 3*d*, Ref:HG19).

Comparative Assessment of Customized Scaffolds Vs. Primary Sequence as an Alignment Reference To further evaluate performance of the custom scaffolds approach, the CBS variant calls to those from single reference genome mapping by analysing NGS data for the 1000 Genomes Project trios, CEPH/UTAH Pedigree NA12878/NA12891/NA12892 and the YRI Pedigree NA19240/NA19239/NA19238 were compared. Sanger sequencing had been used to identify and confirm that the c.833T>C and c.844_845ins68 variants were present in NA12892 (CEPH mother), NA19240 (YRI daughter) and NA19238 (YRI mother). As deduced by Mendelian genetics, the two variants were determined to be in cis in all three cell lines.

Figure 6:
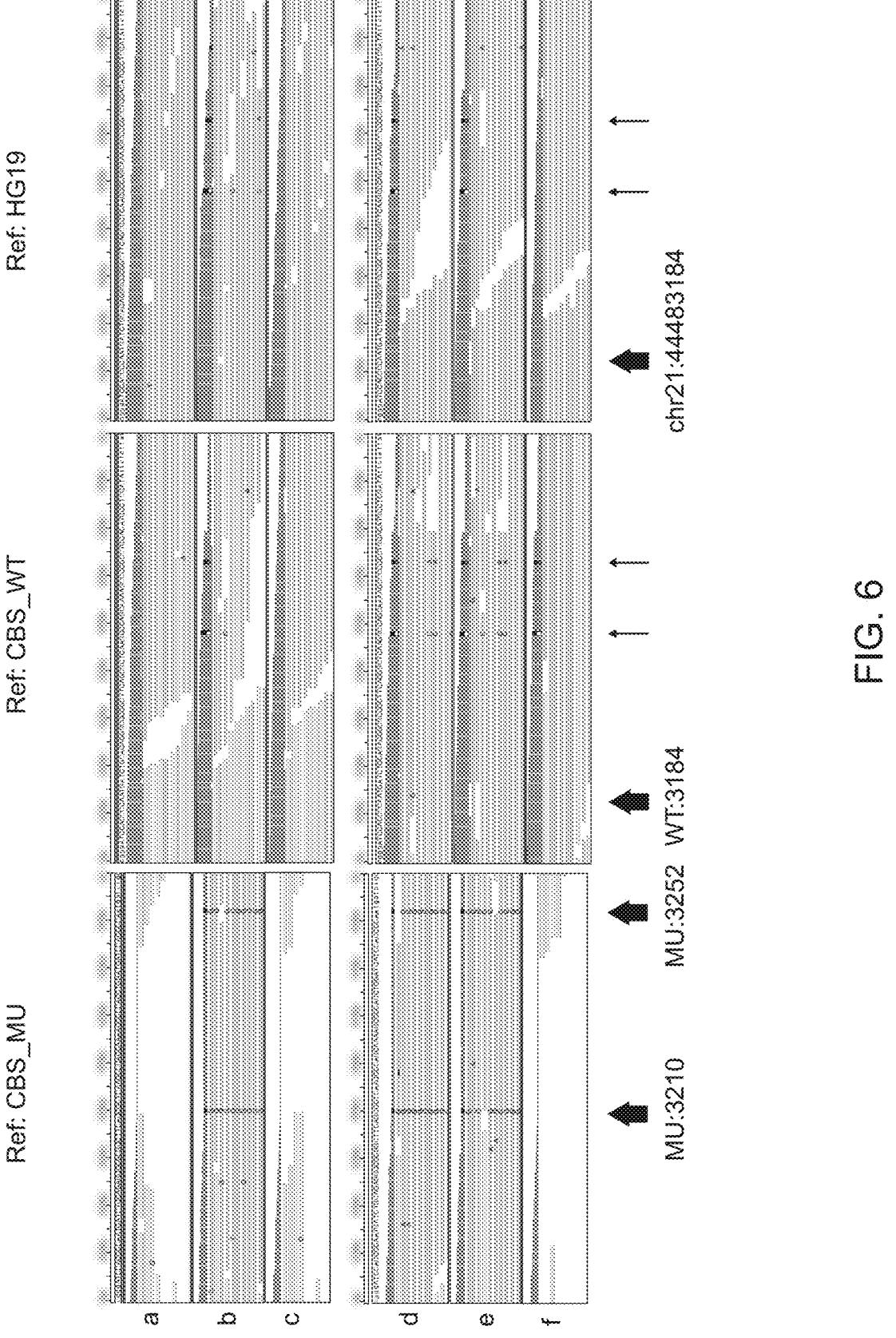
FIG. 6 shows detection of c. [833T>C;844_845ins68] in two 1000G trios using custom scaffolds in accordance with an embodiment of the disclosure. Read alignment on the custom scaffold Ref: CBS MU for the CEPH (a-c) and YRI trio (d-f) are shown.

With custom scaffolds as the references, all three 1000 Genomes Project samples were correctly genotyped for the c.833T>C variant in cis with the 68 bp insertion as indicated by base changes at CBS_MU:3210 and CBS_MU:3252 (FIG. 6, Ref:CBS_MU and Ref:CBS_WT). Thus, FIG. 6 shows detection of c.[833T>C; 844_845ins68] in two 1000G trios using custom scaffolds in accordance with an embodiment of the disclosure. Read alignment on the custom scaffold Ref:CBS_MU for the CEPH (a-c) and YRI trio (d-f) are shown. Characteristic alignment profiles indicate that the CEPH mother (b) and the YRI mother-daughter duo (d,e) carry the c.[833T>C; 844_845ins68] complex variant. With HG19 as the reference, the read alignment profiles are similar for all members of the CEPH and YRI trios (b-e). Arrows point to the informative bases that are used for variant calling. Two divergent bases between the 68 bp insertion and HG19 reference sequence are shown by the smaller arrows. A third divergent base at the end of the insertion sequence is not visible in the alignments due to soft-clipping.

Allele segregation of c.[833T>C; 844_845ins68] in both trios corresponded to the expected Mendelian inheritance pattern, thereby confirming correct phase assignment by the custom scaffolds method. However, when the GRCh37/HG19 build was used as the reference, reads from samples with the c.[833T>C; 844_845ins68] complex variant struggled to map to the reference genome, and only the 68 bp insertion could be detected either directly or inferred as a structural variant in the alignment based on increased read coverage (FIG. 6, Ref:HG19).

A closer examination of the variant data from the 1000 Genomes Project (NCBI 1000 Genomes Browser Phase 3, ver3.7) revealed that the c.[833T>C; 844_845ins68] complex variant was not called for either NA19240 or NA19238; no CBS genotype data for these variants were available for NA12891. The overall population carrier rate for c.833T>C was found to be 0.02% in the 1000 Genomes Project (accessed Nov. 30, 2019), and 0.15% in gnomAD (accessed Nov. 30, 2019); information on the frequency for the complex variant in any of the 1000 Genomes datasets was not available. This apparent inconsistency suggests that the c.833T>C variant likely was missed by the 1000 Genomes Project in the two trios when it occurred in cis with the 68 bp insertion because of the NGS alignment method used. To further explore the NGS data, we employed a second calling method, GATK Haplotypecaller (ver.4), which uses local de novo reassembly of reads instead of existing mapping data to simultaneously detect SNPs and indels for any region with variation. Using GRCh37/HG19 as the reference to realign the assembled reads, the GATK Haplotypecaller correctly called the cis variant in NA19240, NA19238 and NA12891. Thus, without additional analysis methods that can take into account the level of variation for a region, these findings were consistent with the expected limitations for detection of the CBS variants when read alignment was to a standard reference genome.

CBS Variant Analysis with Clinical Specimens Using Customized Scaffolds

Figure 7:
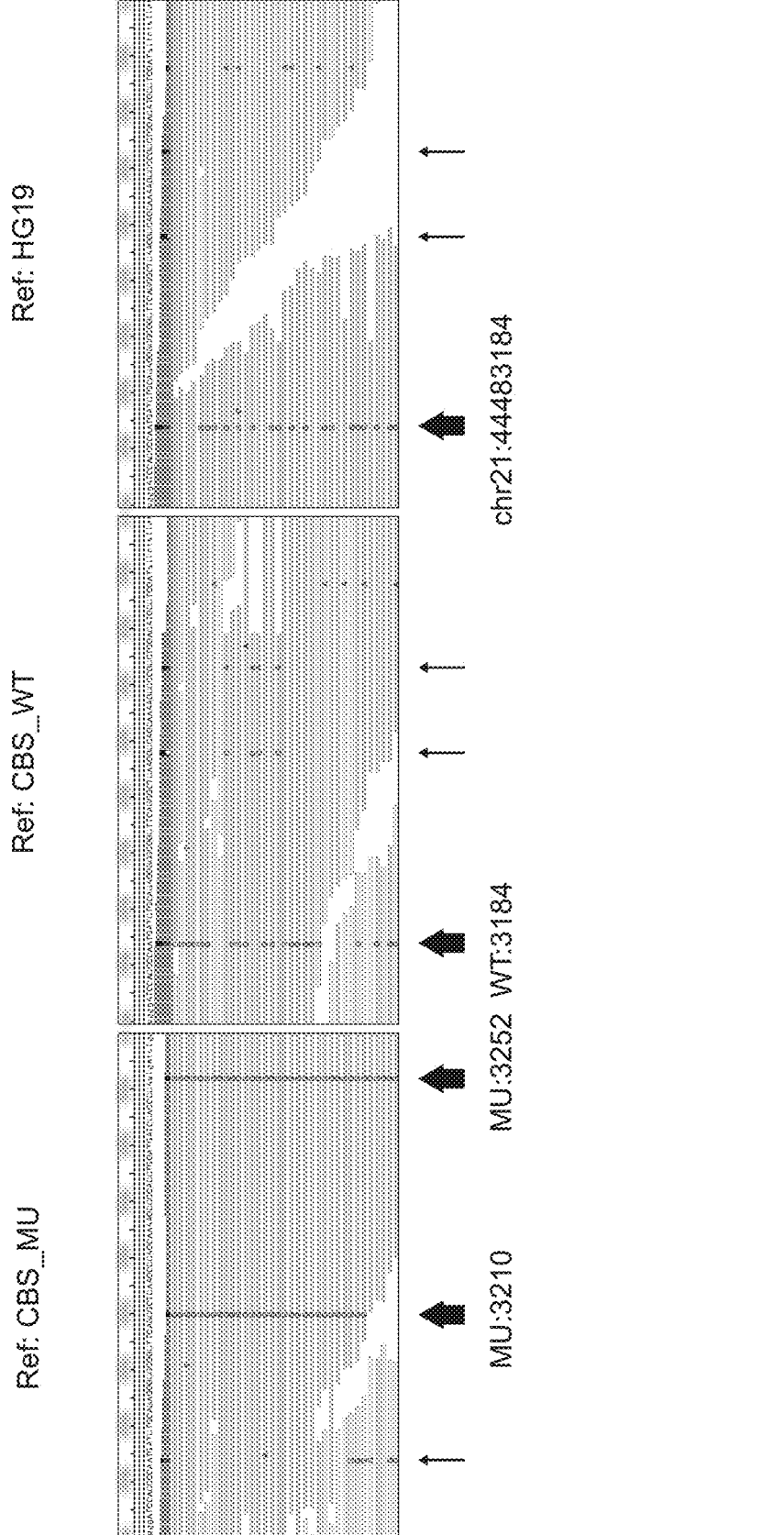
FIG. 7 shows detection of the c.833T>C single nucleotide variant in trans with the complex variant, c. [833T>C; 844_845ins68] in accordance with an embodiment of the disclosure.

The customized scaffolds approach was applied to the analysis of 60,318 consecutive specimens from throughout the United States that had been referred for carrier testing (Table 2). A carrier rate of 18.49% was determined for the c.[833T>C; 844_845ins68] complex variant and 0.17% for the pathogenic c.833T>C variant. The observed carrier rate for c.[833T>C; 844_845ins68] in these experiments is consistent with the reported range for general population frequencies of up to 40% in African/African Americans and less than 1% in Native American populations. For a small number of clinical cases (0.012%), c.833T>C was also detected as part of the benign complex variant c.[833T>C; 844_845ins68] on one chromosome, and as the pathogenic single nucleotide variant c.833T>C on the other (FIG. 7). No incidence of the c.833T>C variant in trans with the 68 bp insertion was observed in our specimen set, which is consistent with published population studies.

FIG. 7 shows detection of the c.833T>C single nucleotide variant in trans with the complex variant, c.[833T>C; 844_845ins68] in accordance with an embodiment of the disclosure. Comparison of read alignments using the custom scaffolds and HG19 genome assembly are shown using Integrative Genomics Viewer for a clinical sample in which the pathogenic variant c.833T>C is heterozygous to the c.[833T>C; 844_845ins68] complex variant. Arrows indicate the locations of the informative bases for variant detection on the scaffolds and HG19. With HG19 as the reference, c.833T>C is clearly detected at the expected coordinate, but not the 68 bp insertion. DNA sequence is shown above the per-base coverage track, and two of the bases known to diverge between the 68 bp insertion and the HG19 reference sequence are shown by the smaller arrows in the Ref:CBS_WT and Ref:HG19 alignments.

TABLE 2

| Ethnicity | Number of Samples | | c.833T > C (%) | | c.[833T > C; 844_845ins68] (%) | |
|---|---|---|---|---|---|---|
| | gnomAD | Current study | gnomAD | Current study | gnomAD | Current study |
| All Ethnicities | 13,970 | 60,318 | 0.17 | 0.17 | 21.10 | 18.49 |
| African/African American | 4,359 | 177 | 0.05 | 0 | 38.72 | 45.20 |
| Latin American | 424 | 323 | 0 | 0 | 12.54 | 16.10 |
| Ashkenazi Jewish | 145 | 169 | 0 | 0 | 7.93 | 10.65 |
| East Asian | 780 | 382 | 0 | 0 | 0.26 | 4.71 |
| European | 7,718 | 518 | 0.29 | 0.39 | 13.70 | 14.29 |
| Other (e.g., mixed ethnicities) | 544 | 292 | 0 | 0 | 14.76 | 16.44 |

Figure 8:
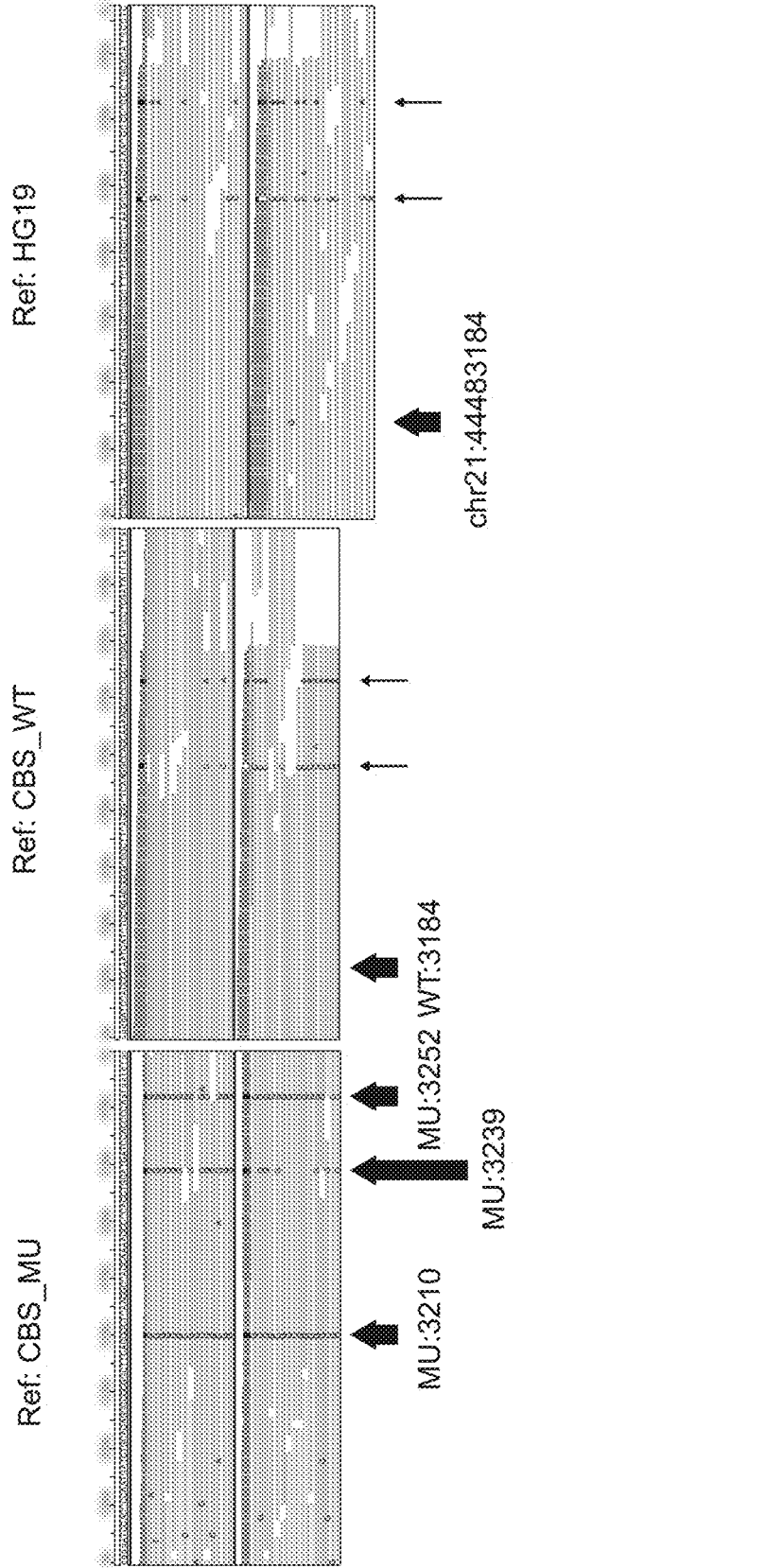
FIG. 8 shows detection of the rare 68 bp insertion in clinical samples via the CBS MU scaffold in accordance with an embodiment of the disclosure. Shown are representative examples of a sample that is heterozygous for a rare allele of the 68 bp insertion (a), and a sample that is a compound heterozygote for the rare and common 68 bp insertion alleles that are both in cis with c.833T>C (b).

A subset of 1861 clinical samples with self-reported ethnicity was further analysed to estimate carrier rates for different groups. As a comparison, the chromosome-based population frequencies for c.833T>C (r55742905) in gnomAD were extracted and converted to carrier rates. Table 2 shows that the overall c.833T>C carrier rates (All Ethnicities) and those for individuals of European ancestry were very similar between gnomAD and this study. Likewise, the population frequencies for the c.[833T>C; 844_845ins68] complex variant among the different ethnic groups analysed in this study were, with the exception of the East Asian group, consistent with frequencies found in gnomAD (Table 2). For the East Asian group, the carrier rate in clinical specimens was much higher than in gnomAD, and closer to the carrier rate previously reported in the Chinese population. In addition, 85 samples of various ethnicities were identified as heterozygous for c.833T>C in cis with the rare 68 bp insertion sequence using the CBS_MU scaffold. Of these, 14 were compound heterozygotes with the c.[833T>C; 844_845ins68] complex variant with the common 68 bp insertion sequence (FIG. 8). Thus, FIG. 8 shows detection of the rare 68 bp insertion in clinical samples via the CBS_MU scaffold. Shown are representative examples of a sample that is heterozygous for a rare allele of the 68 bp insertion (a), and a sample that is a compound heterozygote for the rare and common 68 bp insertion alleles that are both in cis with c.833T>C (b). It can be seen that reads with the rare 68 bp insertion allele are detected by an additional readout at MU:3239 on the Ref:CBS_MU scaffold. Bases indicated by smaller arrows in the Ref:CBS_WT and Ref: HG19 alignments differ between the 68 bp insertion and the HG19 reference sequence. Two other divergent bases in the rare 68 bp insertion allele occur at the very end of the sequence and thus, are soft-clipped and not visible in the alignments. The analysis further demonstrated that the custom scaffolds approach improves the detection and phasing of challenging variants such as the c.833T>C variant and the 68 bp insertion compared with methods that have been used for other population databases (e.g., 1000 Genomes), which failed to identify the c.[833T>C; 844_845ins68] complex variant.

The success of NGS in high-throughput sequence variant detection with human genomic DNA has revolutionized the field of clinical genetic testing in the past few years. NGS performance for the detection of single nucleotide variants and small insertion or deletion variants is highly accurate using the current standard human reference genome build for read alignment. However, the single reference genome approach sometimes falls short for variant detection in regions with duplications, pseudogenes, paralogous genes or complex variants because reads from different haplotypes are forced to align to the same genomic region, leading to false negative and false positive calls. In this study, using two clinically important CBS variants as examples, it was found that that a customized variant-specific scaffold approach enables reads for these complex regions to segregate by haplotypes. Incorporation of a predefined mismatch at a highly conserved base further customizes the mutant scaffold for efficient triaging and phasing of the variant calls. The disclosed custom scaffold alignment method can be easily expanded and adapted to detect other technically challenging target variants without the need for expensive equipment or extensive customization of the computational method. When applied in combination with standard NGS pipelines that utilize the current human reference genome build, the disclosed method can improve the performance of the variant calling process.

The custom scaffold approach makes it possible to determine variant type and obtain phasing information with high sensitivity and accuracy. Using simulated short reads as input, all variant and phasing combinations for the CBS complex variant, c.[833T>C; 844_845ins68], were successfully resolved, thereby improving sensitivity and specificity of the assay. The analysis of two widely studied trios from the 1000 Genomes Project revealed the presence of the c.[833T>C; 844_845ins68] complex variant in a parent-child duo that segregated as expected for a Mendelian inheritance pattern and was concordant with the gold-standard Sanger sequencing results Attempts to detect this variant with a caller that aligned reads directly to a standard genome reference were not successful unless additional algorithms such as those in the GATK Haplotypecaller were employed. It was also not surprising to find that the variant allele frequency for c.833T>C was underestimated when it occurred in cis given that the 68 bp insertion, which also includes the c.833T wild-type base, is almost identical in sequence to the reference genome. Phasing and imputation errors of rare variants in the 1000 Genomes data have been attributed to the limited sample size. The disclosed experiments suggest that the c.[833T>C; 844_845ins68] complex variant may have remained undetected in the 1000 Genomes samples as a result of the alignment methods used in the original NGS analysis, and that there may be other complex or rare variants in these data that also have—gone underreported.

Application of the customized scaffolds to a large cohort of anonymized clinical samples (>60,000 specimens) has provided representative population carrier frequency data for the pathogenic variant c.833T>C and carrier frequency for the benign complex variant c.[833T>C; 844_845ins68]. Since these samples were accrued from carrier testing, ascertainment bias cannot be ruled out, however, as reported by others, c.[833T>C; 844_845ins68] was observed at a much higher frequency (18.49%) than the pathogenic c.833T>C variant (0.17%) in the sample set. The observed overall frequency for c.833T>C was approximately the same as in gnomAD, which consists primarily of healthy individuals and thus, is similar to the clinical cohorts. Furthermore, the allele frequency for c.[833T>C; 844_845ins68] has been reported to vary by more than 100 fold depending on the ethnic population. It was also possible to compare the allele frequencies by ethnicity on a small subset of the samples (~3.1%). Despite the limited number of specimens, the results were consistent with gnomAD for the ethnic populations analysed except East Asians, suggesting that the samples for this group may have a different demographic composition in our dataset. It is also worth noting that although the CBS_MU scaffold was designed with the common 68 bp insertion allele, the c.833T>C variant in cis with the rare c.844_845ins68 allele was detected using this scaffold in 0.14% of the samples. All were heterozygous for c.[833T>C; 844_845ins68], and of these, 0.02% were compound heterozygous with the c.[833T>C; 844_845ins68] complex variant that had the common 68 bp insertion allele, indicating that the disclosed approach can identify and phase other variations of the insertion. Interestingly, within the used cohort, six samples with c.833T>C in trans with c.[833T>C; 844_845ins68] were also identified, giving a genotype frequency of 0.012%. This compound heterozygosity had been previously identified in a patient affected with a mild form of homocystinuria in an Italian cohort, but until now, no genotype frequency information had been reported.

Thus, in an embodiment, the disclosed custom scaffolds alignment approach can accurately call and phase variants using a standard NGS pipeline and the current human reference genome build without the added cost of specialized instruments, reagents or software. While phasing capability is limited to the read length, this approach is especially suited for the detection and phasing of complex structural variants that occur within challenging intragenic regions, e.g., those that are repetitive or highly homologous to other genes. As demonstrated with two clinically important CBS variants, the ability to detect and accurately genotype rare and/or complex variants, especially for clinical tests such as carrier testing, will enable better reproductive risk assessment and will help guide physicians in the management of patient care.

Methods

Cell Lines and Specimens

Cell line DNA of two parent-child trios from the 1000 Genomes Project, representing populations of Northern/Western European ancestry in Utah (CEPH/UTAH; NA12878, NA12891, and NA12892) and the Yoruba in Ibadan, Nigeria (YRI; NA19240, NA19239 and NA19238), were obtained from the Coriell Institute for Medical Research (Camden, NJ). CBS genomic data on clinical specimens, which had been referred for testing on our Inheritest[SM] carrier test panels were obtained at our CLIA-approved clinical testing laboratory (Integrated Genetics, Laboratory Corporation of America® Holdings, Westborough, MA).

All procedures followed were in accordance with the ethical standards of the responsible committee on human experimentation (institutional and national) and with the Helsinki Declaration of 1975, as revised in 2000. Per the US Federal Policy for the Protection of Human Subjects, institutional review board exemption is applicable due to de-identification of the presented data (45 CFR part 46.101(b)(4)). Consent was obtained from all patients by the referring physician at the time that testing was ordered. All specimens were de-identified according to the policies and procedures at Integrated Genetics prior to their use in this study.

Inheritest[SM] Carrier Test NGS Panels

The Inheritest[SM] NGS carrier tests are multigene panels that include the CBS gene. Library preparation and target enrichment were performed using the Agilent SureSelectXT method (Agilent Technologies, Santa Clara, CA). Briefly, the genomic DNA was fragmented by sonication (Covaris, Woburn, MA), followed by end-repair, A-tailing and adaptor ligation. A target enrichment step was carried out using custom-designed Agilent RNA baits to capture ~0.5M bases followed by post-capture indexing of the libraries for multiplex sequencing. Up to 96 libraries were pooled together and paired-end sequenced at 2×150 cycles using either the MiSeqV3 chemistry or the HiSeq2500 Rapid Run mode (Illumina, San Diego, CA) at 15× minimum base coverage. Raw sequencing data were demultiplexed with the Illumina CASAVA v.1.8.2 software to generate fastq sequences for each sample.

Variant Detection

In certain embodiments, customized scaffold may be designed for each challenging variant. Such scaffolds may separate the reads with the variant from reads without the variant to improve detection sensitivity and specificity. Besides the variant of interest, these scaffolds could also include additional design parameters. As an example, for a CBS complex variant with the 68 bp insertion, a base change was introduced into the custom scaffold (inside the 68 bp insertion) to serve as the readout for the presence of the 68 bp insertion. As described in detail herein, having the base change in the scaffold also enables phasing between the 68 bp ins and the point mutation (c.833T>C). Illumina paired-end sequence reads were used as input for an internally developed and validated variant detection workflow using the CLCbio Genomic Server (version 9.1.1) and Workbench software (version 10.1.1) (Qiagen Bioinformatics, Redwood City, CA). This workflow had two branches. The main branch analysed all sequencing reads for the Inheritest[SM] panels by first trimming the reads to remove library adaptor sequences and low quality bases (Q20 minimum quality threshold), and then aligning them to GRCh37/HG19 human genome build, followed by duplicate reads removal, local realignment, variant detection and annotation. For detection and phasing of the CBS variants c.833T>C and c.[833T>C; 844_845ins68], a second workflow branch for read alignment to two custom scaffolds was implemented after the read trimming step. The first scaffold, CBS_WT, was identical to the HG19 reference region chr21:44480001-44485000. The second scaffold, CBS_MU, was also from the same region, but included the common 68 bp insertion plus an introduced G>C base change within the 68 bp insertion that served as a marker to detect the insertion. After read mapping to the scaffolds, duplicate reads were removed prior to variant analysis and phasing determination. The output from this workflow branch was fed into the main branch output to create the final variant report.

Analysis of the two CBS variants in the 1000 Genomes trios was also carried out using the Haplotypecaller in the Genome Analysis Toolkit (GATK ver. 4.0; Broad Institute, Cambridge, MA) following the recommended GATK Best Practices, and using GRCh37/HG19 build as the reference sequence. Alignment of simulated reads was visualized using Integrative Genomics Viewer (IGV, Broad Institute, Cambridge, MA).

Simulation of Variant Reads

An in-house Python script was developed to generate simulated variant reads utilizing the ART package, which uses platform-specific error models and base quality profiles for read simulation. The parameters for paired read simulations used in this study were as follows: 200× coverage, 150 bp read length, 300 bp fragment size, 100 bp fragment size standard deviation, and Illumina HiSeq error model. The input sequence template for simulation with the ART tool represented all possible genotype and phasing combinations of the two CBS targeted variants, c.833T>C and c.844_845 ins68, as well as 500 additional flanking bases on either side of the targeted variants. All genotype combinations of c.833T>C and c.844_845 ins68 used in simulation input had been confirmed to report the correct genotype assignment after variant calling.

Sanger Confirmation

CBS variants detected by NGS were confirmed by Sanger sequencing with internally designed target-specific, M13-tagged primers:

```
Forward:
                                        (SEQ ID NO: 4)
5'-TGTAAAACGACGGCCAGTCCACCACCCACAGGCAGAT-3'

Reverse:
                                        (SEQ ID NO: 5)
5'-CAGGAAACAGCTATGACCGCGGGGCTTGCCCTTCTGTT-3'.
```

PCR amplification was performed using 0.25 U AmpliTaq Gold DNA polymerase (ThermoFisher Scientific, Waltham, MA) in 1×PCR Buffer II, 1.5 mM $MgCl_2$, 50 uM dNTPs, and 250 nM primers and the following cycling condition: 1 cycle at 95° C. for 10 min; 35 cycles of denaturation at 95° C. for 20 s, annealing at 60° C. for 30 s and extension at 72° C. for 60 s; 1 cycle at 72° C. for 3 min. Sanger sequencing was carried out using BigDye™ Terminator v3.1 Cycle Sequencing kit (ThermoFisher Scientific, Waltham, MA). Capillary electrophoresis on the ABI3730XL (ThermoFisher Scientific, Waltham, MA). SeqScape v2.5 (ThermoFisher Scientific, Waltham, MA) was used for the sequence analysis and visualization.

That which is claimed:

1. A computer-implemented method for detecting the presence or absence of a complex genetic variant in a sample, comprising:

accessing a mutant scaffold that comprises a custom nucleotide sequence that includes: (i) a mutation characteristic of the complex genetic variant within a target region of a genome and (ii) an additional artificial genetic variation not found in either the complex genetic variant or any wild-type sequence within the target region of the genome, wherein the mutant scaffold is constructed in silico as a digital structure representation of the custom nucleotide sequence;

accessing a wild-type scaffold that comprises a wild-type nucleotide sequence within the target region of the genome, wherein the wild-type scaffold is constructed in silico as a digital structure representation of the wild-type nucleotide sequence;

accessing sequence reads of nucleic acid obtained from the sample for the target region;

mapping, by an alignment algorithm, the sequence reads to matching sequences within the digital structure representation of the custom nucleotide sequence of the mutant scaffold;

mapping, by the alignment algorithm, the sequence reads to matching sequences within the digital structure representation of the wild-type nucleotide sequence of the wild-type scaffold;

counting (i) sequence reads mapped to the custom nucleotide sequence that includes the complex genetic variant and the additional artificial genetic variation and (ii) sequence reads mapped to the wild-type nucleotide sequence, wherein the counting generates a quantification of the sequence reads mapped to the custom nucleotide sequence and a quantification of the sequence reads mapped to the wild-type nucleotide sequence;

determining whether the sample contains the mutation based on the quantification of the sequence reads mapped to the custom nucleotide sequence versus the quantification of the sequence reads mapped to the wild-type nucleotide sequence; and outputting a result that the sample contains the presence or absence of the complex genetic variant based on the determination of whether the sample contains the mutation.

2. The computer-implemented method of claim 1, wherein:

the additional artificial genetic variation serves as a marker for the presence and/or phasing of the mutation characteristic of the complex genetic variant; and mapping the sequence reads to matching the sequences within the digital structure representation of the custom nucleotide sequence comprises identifying an expected mismatch between the sequence reads and the matching sequences based on the additional artificial genetic variation.

3. The computer-implemented method of claim 1, further comprising parametrizing the alignment algorithm with a mismatch and gap penalty cost difference such that only the sequence reads that have the mutation characteristic of the complex genetic variant will align to the mutant scaffold.

4. The computer-implemented method of claim 1, further comprising:

determining the sample contains the mutation characteristic of the complex genetic variant based on the quantification of the sequence reads mapped to the sequences that include the complex genetic variant versus the quantification of the sequence reads mapped to the sequences that include the wild-type nucleotide sequence;

outputting the result that the sample contains the presence of the complex genetic variant based on the determination that the sample contains the mutation characteristic of the complex genetic variant; and providing a treatment to a subject associated with the sample in accordance with the presence of the complex genetic variant in the sample.

5. The computer-implemented method of claim 4, wherein the treatment is a therapeutic agent or a prescribed dietary change.

6. The computer-implemented method of claim 1, further comprising providing a treatment to a subject associated with the sample in accordance with the presence of the complex genetic variant in the sample, wherein the complex genetic variant is in the target region of a cystathionine beta-synthase (CBS) gene, wherein the treatment is a therapeutic agent or a prescribed dietary change, and wherein the therapeutic agent is vitamin B6 or the prescribed dietary change is a low-methionine diet.

7. The computer-implemented method of claim 1, wherein the complex genetic variant has two mutations.

8. The computer-implemented method of claim 7, further comprising:

determining whether the two mutations are on the same chromosome (cis) or on different chromosomes (trans) based on the mapping of the sequence reads to the matching sequences in the mutant scaffold; and outputting the result that the sample contains the presence or absence of the complex genetic variant with notation concerning the two mutations being on the same chromosome (cis) or on different chromosomes (trans) based on the determination of whether the sample contains the mutation characteristic of the complex genetic variant and whether the two mutations are on the same chromosome (cis) or on different chromosomes (trans).

9. The computer-implemented method of claim 1, wherein the complex genetic variant is in the target region of a cystathionine beta-synthase (CBS) gene.

10. The computer-implemented method of claim 9, wherein the mutant scaffold and wild-type scaffold distinguish (i) a sequence having a 68 bp insertion [844_845ins68] in cis with a c.833T>C mutation, from (ii) a sequence having the 68 bp insertion [844_845ins68] in trans with c.833T>C, from (iii) a sequence having the 68 bp insertion [844_845ins68] without c.833T>C, or from (iv) a sequence having c.833T>C without the 68 bp insertion [844_845ins68].

11. A system comprising:

one or more processors;

a memory coupled to the one or more processors, the memory storing a plurality of instructions executable by the one or more processors, the plurality of instructions comprising instructions that when executed by the one or more processors cause the one or more processors to perform processing comprising:

accessing a mutant scaffold that comprises a custom nucleotide sequence that includes: (i) a mutation characteristic of a complex genetic variant within a target region of a genome, and (ii) an additional artificial genetic variation not found in either the complex genetic variant or any wild-type sequence within the target region of the genome, wherein the mutant scaffold is constructed in silico as a digital structure representation of the custom nucleotide sequence;

accessing a wild-type scaffold that comprises a wild-type nucleotide sequence within the target region of the genome, wherein the wild-type scaffold is constructed in silico as a digital structure representation of the wild-type nucleotide sequence;

accessing sequence reads of nucleic acid obtained from a sample for the target region;

mapping, by an alignment algorithm, the sequence reads to matching sequences within the digital structure representation of the custom nucleotide sequence of the mutant scaffold;

mapping, by the alignment algorithm, the sequence reads to matching sequences within the digital structure representation of the wild-type nucleotide sequence of the wild-type scaffold;

counting (i) sequence reads mapped to the custom nucleotide sequence that includes the complex genetic variant and the additional artificial genetic variation and (ii) sequence reads mapped to the wild-type nucleotide sequence, wherein the counting generates a quantification of the sequence reads mapped to the custom nucleotide sequences and a quantification of the sequence reads mapped to the wild-type nucleotide sequence;

determining whether the sample contains the mutation based on the quantification of the sequence reads mapped to the custom nucleotide sequences versus the quantification of the sequence reads mapped to the wild-type nucleotide sequence; and outputting a result that the sample contains the presence or absence of the complex genetic variant based on the determination of whether the sample contains the mutation.

12. The system of claim 11, wherein:

the additional artificial genetic variation serves as a marker for the presence and/or phasing of the mutation characteristic of the complex genetic variant; and mapping the sequence reads to matching the sequences within the digital structure representation of the custom nucleotide sequence comprises identifying an expected mismatch between the sequence reads and the matching sequences based on the additional artificial genetic variation.

13. The system of claim 11, wherein the processing further comprises parametrizing the alignment algorithm with a mismatch and gap penalty cost difference such that only the sequence reads that have the mutation characteristic of the complex genetic variant will align to the mutant scaffold.

14. The system of claim 11, wherein the processing further comprises: determining the sample contains the mutation characteristic of the complex genetic variant based on the quantification of the sequence reads mapped to the sequences that include the complex genetic variant versus the quantification of the sequence reads mapped to the sequences that include the wild-type nucleotide sequence; outputting the result that the sample contains the presence of the complex genetic variant based on the determination that the sample contains the mutation characteristic of the complex genetic variant; and outputting a treatment recommendation for a subject associated with the sample in accordance with the presence of the complex genetic variant in the sample.

15. The system of claim 11, wherein the complex genetic variant has two mutations and the processing further comprises:

determining whether the two mutations are on the same chromosome (cis) or on different chromosomes (trans) based on the mapping of the sequence reads to the matching sequences in the mutant scaffold; and outputting the result that the sample contains the presence or absence of the complex genetic variant with notation concerning the two mutations being on the same chromosome (cis) or on different chromosomes (trans) based on the determination of whether the sample contains the mutation characteristic of the complex genetic variant and whether the two mutations are on the same chromosome (cis) or on different chromosomes (trans).

16. A computer-program product tangibly embodied in a non-transitory machine-readable storage medium, including instructions configured to cause one or more data processors to perform actions including:

accessing a mutant scaffold that comprises a custom nucleotide sequence that includes: (i) a mutation characteristic of a complex genetic variant within a target region of a genome and (ii) an additional artificial genetic variation not found in either the complex genetic variant or any wild-type sequence within the target region of the genome, wherein the mutant scaffold is constructed in silico as a digital structure representation of the custom nucleotide sequence;

accessing a wild-type scaffold that comprises a wild-type nucleotide sequence within the target region of the genome, wherein the wild-type scaffold is constructed in silico as a digital structure representation of the wild-type nucleotide sequence;

accessing sequence reads of nucleic acid obtained from a sample for the target region;

mapping, by an alignment algorithm, the sequence reads to matching sequences within the digital structure representation of the custom nucleotide sequence of the mutant scaffold;

mapping, by the alignment algorithm, the sequence reads to matching sequences within the digital structure representation of the wild-type nucleotide sequence of the wild-type scaffold;

counting (i) sequence reads mapped to the custom nucleotide sequence that includes the complex genetic variant and the additional artificial genetic variation and (ii) sequence reads mapped to the wild-type nucleotide sequence, wherein the counting generates a quantification of the sequence reads mapped to the custom nucleotide sequences and a quantification of the sequence reads mapped to the wild-type nucleotide sequence;

determining whether the sample contains the mutation based on the quantification of the sequence reads mapped to the custom nucleotide sequence versus the quantification of the sequence reads mapped to the wild-type nucleotide sequence; and outputting a result that the sample contains the presence or absence of the complex genetic variant based on the determination of whether the sample contains the mutation.

17. The computer-program product of claim 16, wherein:

the additional artificial genetic variation serves as a marker for the presence and/or phasing of the mutation characteristic of the complex genetic variant; and mapping the sequence reads to matching the sequences within the digital structure representation of the custom nucleotide sequence comprises identifying an expected mismatch between the sequence reads and the matching sequences based on the additional artificial genetic variation.

18. The computer-program product of claim 16, wherein the actions further comprise parametrizing the alignment algorithm with a mismatch and gap penalty cost difference such that only the sequence reads that have the mutation characteristic of the complex genetic variant will align to the mutant scaffold.

19. The computer-program product of claim 16, wherein the actions further comprise: determining the sample contains the mutation characteristic of the complex genetic variant based on the quantification of the sequence reads mapped to the sequences that include the complex genetic variant versus the quantification of the sequence reads mapped to the sequences that include the wild-type nucleotide sequence; outputting the result that the sample contains the presence of the complex genetic variant based on the determination that the sample contains the mutation characteristic of the complex genetic variant; and outputting a treatment recommendation for a subject associated with the sample in accordance with the presence of the complex genetic variant in the sample.

20. The computer-program product of claim 16, wherein the complex genetic variant has two mutations and the actions further comprise:

determining whether the two mutations are on the same chromosome (cis) or on different chromosomes (trans) based on the mapping of the sequence reads to the matching sequences in the mutant scaffold; and outputting the result that the sample contains the presence or absence of the complex genetic variant with notation concerning the two mutations being on the same chromosome (cis) or on different chromosomes (trans) based on the determination of whether the sample contains the mutation characteristic of the complex genetic variant and whether the two mutations are on the same chromosome (cis) or on different chromosomes (trans).

\*    \*    \*    \*    \*